US007772352B2

(12) United States Patent
Bezwada

(10) Patent No.: US 7,772,352 B2
(45) Date of Patent: Aug. 10, 2010

(54) BIOABSORBABLE AND BIOCOMPATIBLE POLYURETHANES AND POLYAMIDES FOR MEDICAL DEVICES

(75) Inventor: Rao S. Bezwada, Whitehouse Station, NJ (US)

(73) Assignee: Bezwada Biomedical LLC, Hillsborough, NJ (US)

( * ) Notice: Subject to any disclaimer, the term of this patent is extended or adjusted under 35 U.S.C. 154(b) by 926 days.

(21) Appl. No.: 11/255,050

(22) Filed: Oct. 20, 2005

(65) Prior Publication Data

US 2006/0188547 A1    Aug. 24, 2006

Related U.S. Application Data

(63) Continuation-in-part of application No. 11/233,876, filed on Sep. 23, 2005, now Pat. No. 7,691,364, and a continuation-in-part of application No. 11/220,044, filed on Sep. 6, 2005.

(60) Provisional application No. 60/647,996, filed on Jan. 28, 2005.

(51) Int. Cl.
*C08G 18/77* (2006.01)
*C08G 18/78* (2006.01)
*C08L 75/04* (2006.01)
*A61K 31/00* (2006.01)
*A61K 47/14* (2006.01)

(52) U.S. Cl. ............ 528/44; 424/78.08; 424/78.37; 514/785; 514/788; 521/155; 521/159; 525/440; 525/454; 528/59; 560/103; 560/106; 560/110; 560/112; 560/142; 560/145; 560/179; 560/180; 560/186; 560/196; 560/254; 560/330; 560/359

(58) Field of Classification Search ............... 528/44, 528/59; 560/330, 103, 106, 110, 112, 142, 560/145, 179, 180, 186, 196, 254, 359; 424/78.08, 424/78.37; 514/758, 788; 521/155, 159; 525/440, 454; 604/890.1, 891.1; 623/11, 623/66

See application file for complete search history.

(56) References Cited

U.S. PATENT DOCUMENTS

| | | | | |
|---|---|---|---|---|
| 3,492,332 A | * | 1/1970 | Ulrich et al. ................. 560/30 |
| 4,740,534 A | | 4/1988 | Matsuda et al. ............. 523/111 |
| 4,829,099 A | * | 5/1989 | Fuller et al. ................. 606/214 |
| 4,994,542 A | | 2/1991 | Matsuda et al. ............... 528/70 |
| 5,173,301 A | | 12/1992 | Itoh et al. .................... 424/448 |
| 5,552,507 A | * | 9/1996 | Wamprecht et al. .......... 528/44 |
| 6,894,140 B2 | | 5/2005 | Roby ........................... 528/70 |

FOREIGN PATENT DOCUMENTS

EP    0 295 055 A2    12/1988

OTHER PUBLICATIONS

Bruin et al., "Design and synthesis of biodegradable poly(esterurethane) alastomer networks composed of non-toxic building blocks," Makromol Chem., Rapid Commun.9,589-594 (1988).

* cited by examiner

*Primary Examiner*—Rabon Sergent
(74) *Attorney, Agent, or Firm*—Fox Rothschild LLP; Peter J. Butch, III; Shahnam Sharareh

(57) ABSTRACT

Absorbable polyurethanes, polyamides and polyester urethanes prepared from at least one compound selected from:

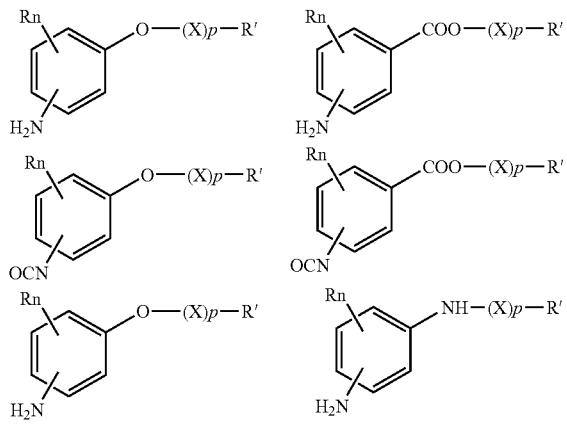

or the diamines and diisocyanates thereof, wherein each X represents a member independently selected from —CH$_2$COO— (glycolic acid moiety), —CH(CH$_3$)COO— (lactic acid moiety), —CH$_2$CH$_2$OCH$_2$COO— (dioxanone), —CH$_2$CH$_2$CH$_2$CH$_2$CH$_2$COO— (caprolactone moiety), —(CH$_2$)$_y$COO— where y is one of the numbers 2, 3, 4 or 6-24 inclusive, and —(CH$_2$CH$_2$O)$_{z'}$CH$_2$COO— where z' is an integer between 2 and 24, inclusive; each Y represents a member independently selected from —COCH$_2$O— (glycolic ester moiety), —COCH(CH$_3$)O— (lactic ester moiety), —COCH$_2$OCH$_2$CH$_2$O— (dioxanone ester), —COCH$_2$CH$_2$CH$_2$CH$_2$CH$_2$O— (caprolactone ester), —CO(CH$_2$)$_m$O— where m is an integer between 2, 3, 4 or 6-24 inclusive, —COCH$_2$O(CH$_2$CH$_2$O)$_n$— where n is an integer between 2 and 24, inclusive; R' is hydrogen, benzyl or an alkyl group, the alkyl group being either straight-chained or branched; p is an integer between 1 and 4, inclusive; and Rn represents one or more members selected from H, alkoxy, benzyloxy, aldehyde, halogen, carboxylic acid and —NO$_2$, which is attached directly to an aromatic ring or attached through an aliphatic chain. Absorbable polymers prepared from these compounds are useful for drug delivery, tissue engineering, tissue adhesives, adhesion prevention and other implantable medical devices.

16 Claims, No Drawings ial Patent Application Ser. No. 60/647,996 filed Jan. 28, 2005 and under 35 U.S.C. § 120 as a Continuation-In Part of U.S. patent application Ser. No. 11/220,044 filed Sep. 6, 2005. The present application also claims priority benefit under 35 U.S.C. § 120 as a Continuation-In-Part of U.S. patent application Ser. No. 11/233,876 filed Sep. 23, 2005 now U.S. Pat. No. 7,691,364. The disclosures of all three applications are incorporated herein by reference in their entireties.

BIOABSORBABLE AND BIOCOMPATIBLE POLYURETHANES AND POLYAMIDES FOR MEDICAL DEVICES

CROSS-REFERENCE TO RELATED APPLICATIONS

The present application claims priority benefit under 35 U.S.C. §119(e) of U.S. Provisional Patent Application Ser. No. 60/647,996 filed Jan. 28, 2005 and under 35 U.S.C. § 120 as a Continuation-In Part of U.S. patent application Ser. No. 11/220,044 filed Sep. 6, 2005. The present application also claims priority benefit under 35 U.S.C. § 120 as a Continuation-In-Part of U.S. patent application Ser. No. 11/233,876 filed Sep. 23, 2005 now U.S. Pat. No. 7,691,364. The disclosures of all three applications are incorporated herein by reference in their entireties.

FIELD OF THE INVENTION

The present invention relates to the discovery of a new class of amines, isocyanates and bioabsorbable polyurethanes, polyester urethanes and polyamides prepared there from. The resultant absorbable polymers are useful for drug delivery, tissue engineering, tissue adhesives, adhesion prevention and other implantable medical devices. In addition, these absorbable polymers should have a controllable degradation profile.

BACKGROUND OF THE INVENTION

Biodegradable polymers have become increasingly important for a variety of biomedical applications including tissue engineering scaffolds. However, relatively few biodegradable, particularly elastomeric, polymers have been developed which are presently in use.

Polymeric medical devices which intentionally degrade and disappear upon completion of their function may mitigate the inevitable, usually negative physiologic responses (eg. fibrous encapsulation) which may limit long-term device success. Thus, an array of degradable polymers have been developed and studied for many uses. However, relatively few of these degradable materials are elastomeric polymers. Rather, the majority of degradable polymers are essentially hard, brittle materials for drug delivery uses. With the increasing interest in tissue engineering degradable materials exhibiting a wide variety of physical properties are necessary to integrate with the various tissues of the body.

Segmented polyurethane elastomers have enjoyed wide use as biomaterials due to their excellent mechanical properties and great chemical versatility. The vast majority of research devoted to the development of biomedical polyurethanes has focused on long-term applications such as vascular grafts and pacemaker lead insulators.

Despite the progress thus far in the development of polyurethanes, relatively little research has been directed at developing intentionally degradable polyurethanes for temporary implantation. Several papers were published in the early 1980's describing polyurethane/polylactide blends as degradable materials for skin substitutes, vascular prostheses and nerve regeneration guides. However, in these cases the polyurethane portion of the blend was non-degradable and served only to provide favorable mechanical properties. Subsequent work by Bruin et al., "Design and Synthesis of Biodegradable Poly(Ester-Urethane) Elastomer Networks Composed of Non-Toxic Building Blocks," *Makromol. Chem., Rapid Commun.*, 9, 584-594, (1988) involved the synthesis of crosslinked polyurethane networks incorporating lactide or glycolide and .epsilon.-caprolactone joined by a lysine-based diisocyanate. These polymers displayed good elastomeric properties and were found to degrade within 26 weeks in vitro and 12 weeks in vivo (subcutaneous implantation in guinea pigs).

However, a drawback of this approach is that the highly crosslinked polymer may not be processed by standard techniques such as solution casting or melt processing as is the case for typical linear, segmented polyurethanes. Cohn et al developed a series of elastomeric polyester-polyether-polyurethane block copolymers intended for use as surgical articles (EP295,055). However, these polymers are relatively stiff, low tensile strength materials, which may preclude their use as elastomeric biomaterials.

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that, in order for surgical adhesives to be accepted by surgeons, they must possess a number of properties. First, they must exhibit high initial tack and an ability to bond rapidly to living tissue. Secondly, the strength of the bond should be sufficiently high to cause tissue failure before bond failure. Thirdly, the adhesive should form a bridge, preferably a permeable flexible bridge. Fourthly, the adhesive bridge and/or its metabolic products should not cause local histotoxic or carcinogenic effects.

Isocyanate-based adhesive/sealant compositions are disclosed, for example, in U.S. Pat. Nos. 6,894,140; 5,173,301; 4,994,542; and 4,740,534, the disclosures of which are incorporated herein in their entirety by this reference.

A number of adhesive systems such as alkyl cyanoacrylates, polyacrylates, maleic anhydride/methyl vinyl ethers, epoxy systems, polyvinyl alcohols, formaldehyde and gluteraldehyde resins and isocyanates have been investigated as possible surgical adhesives. None has gained acceptance because each fails to meet one or more of the criteria noted above. The principal criticism of these adhesives systems has been the slow rate of reaction and potential toxicity problems they pose.

BRIEF SUMMARY OF THE INVENTION

Therefore, the object of the present invention is to provide novel materials that are useful for drug delivery, tissue engineering, tissue adhesives, adhesion prevention and other implantable medical devices.

A further object of the present invention is to provide novel polyamides which are biodegradable and biocompatible.

A further object of the present invention is to provide novel polyurethanes which are biodegradable and biocompatible.

A further object of the present invention is to provide novel polyurethanes, polyamides, polyester urethanes which are biodegradable and biocompatible for tissue engineering.

A further object of the present invention is to provide novel safe, biocompatible and bioabsorbable isocyanate-based adhesives and in particular metabolically-acceptable surgical adhesives. It would also be desirable to provide safe, bicompatible surgical adhesives which are biodegradable. It would also be desirable to provide a method for closing wounds in living tissue by use of novel, metabolically-acceptable surgical adhesives which are low in toxicity as a consequence of their physical properties.

A further object of the present invention is to provide novel polyurethanes of the segmented variety which are bioabsorbable.

A further object of the present invention is to provide a chain extender for use in the formation of biodegradable polyurethanes.

Briefly stated, the present invention relates to the discovery of a new class of amines, isocyanates and bioabsorbable polurethanes, polyamides and polyesterurethanes derived there from. The resultant absorbable polymers are useful for drug delivery, tissue engineering, tissue adhesives, adhesion prevention and other implantable medical devices. In addition, these absorbable polymers should have a controllable degradation profile.

Accordingly, one aspect of the present invention is to prepare an absorbable polymer from at least one compound selected from:

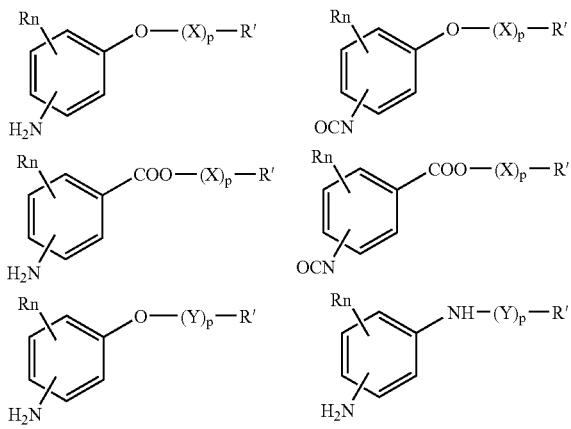

Wherein each X represents a member independently selected from:
- —$CH_2COO$— (glycolic acid moiety),
- —$CH(CH_3)COO$— (lactic acid moiety),
- —$CH_2CH_2OCH_2COO$— (dioxanone moiety),
- —$CH_2CH_2CH_2CH_2CH_2COO$— (caprolactone moiety),
- —$(CH_2)_yCOO$— where y is one of the numbers 2,3,4 or 6-24 inclusive, and
- —$(CH_2CH_2O)_{z'}CH_2COO$— where z' is an integer between 2 and 24, inclusive;

each Y represents a member independently selected from:
- —$COCH_2O$— (glycolic ester moiety),
- —$COCH(CH_3)O$— (lactic ester moiety),
- —$COCH_2OCH_2CH_2O$— (dioxanone ester moiety),
- —$COCH_2CH_2CH_2CH_2CH_2O$— (caprolactone ester moiety),
- —$CO(CH_2)_mO$— where m is an integer between 2-4 and 6-24 inclusive, and
- —$COCH_2O(CH_2CH_2O)_n$— where n is an integer between 2 and 24, inclusive;

R' is hydrogen, benzyl or an alkyl group, the alkyl group being either straight-chained or branched; and p is an integer between 1 and 4, inclusive; and Rn represents one or more members selected from H, alkoxy, benzyloxy, aldehyde, halogen, carboxylic acid and —$NO_2$, which is attached directly to an aromatic ring or attached through an aliphatic chain.

The aromatic compound is selected from amine and/or carboxylic acid containing phenols, such as amino phenols, amino salicylic acids and amino benzoic acids.

Accordingly, another aspect of the present invention is to prepare absorbable polyamides from at least one compound of the formula:

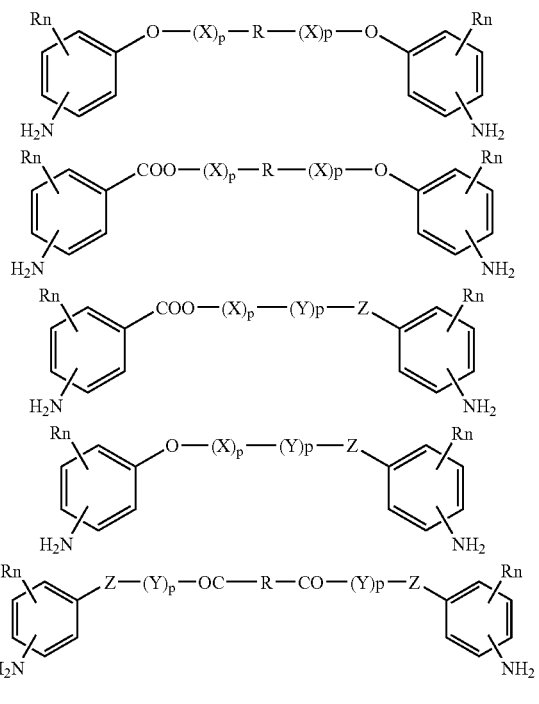

Wherein each X represents a member independently selected from:
- —$CH_2COO$— (glycolic acid moiety);
- —$CH(CH_3)COO$— (lactic acid moiety);
- —$CH_2CH_2OCH_2COO$— (dioxanone moiety);
- —$CH_2CH_2CH_2CH_2CH_2COO$— (caprolactone moiety);
- —$(CH_2)_yCOO$— where y is one of the numbers 2,3,4 and 6-24 inclusive; and
- —$(CH_2CH_2O)_{z'}CH_2COO$— where z' is an integer between 2 and 24, inclusive;

each Y represents a member independently selected from:
- —$COCH_2O$— (glycolic ester moiety);
- —$COCH(CH_3)O$— (lactic ester moiety);
- —$COCH_2OCH_2CH_2O$— (dioxanone ester moiety);
- —$COCH_2CH_2CH_2CH_2CH_2O$— (caprolactone ester moiety);
- —$CO(CH_2)_mO$— where m is an integer between 2-4 and 6-24 inclusive; and
- —$COCH_2O(CH_2CH_2O)_n$— where n is an integer between 2 and 24, inclusive;

each R' is independently a hydrogen, benzyl or an alkyl group, the alkyl group being either straight-chained or branched, each p is independently an integer between 1 and 4, inclusive, Z is O or NH; and Rn represents one or more members selected from H, alkoxy, benzyloxy, aldehyde, halogen, carboxylic acid and —$NO_2$, which is attached directly to an aromatic ring or attached through an aliphatic chain.

The aromatic compound is selected from of amine and/or carboxylic acid containing phenols, such as amino phenols, amino salicylic acids and amino benzoic acids.

Another aspect of the present invention is to prepare an absorbable polyurethane from at least one compound of the formula:

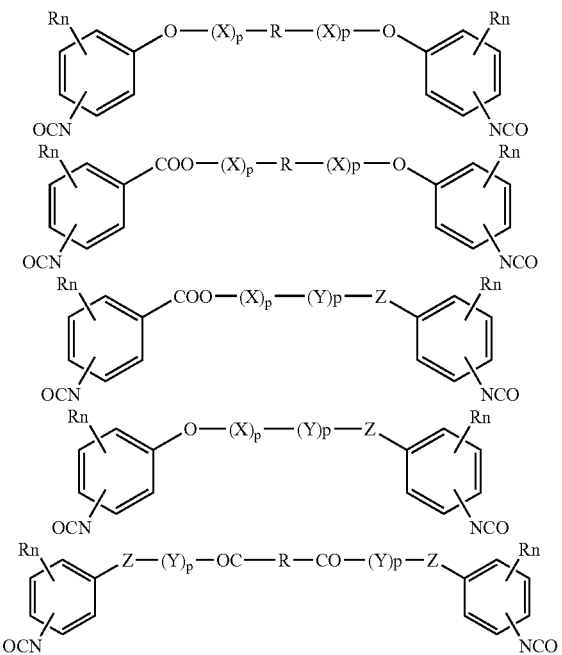

Wherein each X represents a member independently selected from:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is one of the numbers 2,3,4 and 6-24 inclusive; and
—(CH$_2$CH$_2$O)$_{z'}$CH$_2$COO— where z' is an integer between 2 and 24, inclusive;

each Y represents a member independently selected from:
—COCH$_2$O— (glycolic ester moiety);
—COCH(CH$_3$)O— (lactic ester moiety);
—COCH$_2$OCH$_2$CH$_2$O— (dioxanone ester moiety);
—COCH$_2$CH$_2$CH$_2$CH$_2$CH$_2$O— (caprolactone ester moiety);
—CO(CH$_2$)$_m$O— where m is an integer between 2-4 and 6-24 inclusive; and
—CO CH$_2$O(CH$_2$CH$_2$O)$_n$— where n is an integer between 2 and 24, inclusive;
each R' is hydrogen, benzyl or an alkyl group, the alkyl group being either straight-chained or branched; and each p is independently an integer between 1 and 4, inclusive, Z is O or NH; and
Rn represents one or more members selected from H, alkoxy, benzyloxy, aldehyde, halogen, carboxylic acid and —NO$_2$, which is attached directly to an aromatic ring or attached through an aliphatic chain.

The aromatic compound is selected from amine and/or carboxylic acid containing phenols, such as amino phenols, amino salicylic acids and amino benzoic acids.

A further object of the present invention is to provide novel safe, biocompatible and bioabsorbable isocyanate-based adhesives and in particular metabolically-acceptable surgical adhesives. It would also be desirable to provide safe, biocompatible surgical adhesives which are biodegradable. It would also be desirable to provide a method for closing wounds in living tissue by use of novel, metabolically-acceptable surgical adhesives which are low in toxicity as a consequence of their physical properties. A further object of the present invention is to provide novel polyurethanes which are biodegradable and biocompatible.

Another object of the present invention is to provide NCO-terminated hydrophilic polyurethane prepolymer prepared from at least one compound of the formula and a polyol.

DETAILED DESCRIPTION OF THE INVENTION

The present invention thus provides of a new class of amines, isocyanates and bioabsorbable polurethanes, polyamides and polyesterurethanes polymerized therefrom. The resultant absorbable polymers are useful for drug delivery, tissue engineering, tissue adhesives, adhesion prevention and other implantable medical devices. In addition these absorbable polymers should have controllable degradation profile.

The term "bioabsorbable" is defined as those classes of materials that readily react or enzymatically degrade upon exposure to bodily tissue for a relatively short period of time, thus experiencing a significant weight loss in that short time period. Complete bioabsorption should take place within twelve months, although preferably bioabsorption will be complete within nine months and most preferably within six months. In this manner, the polymers of this invention can be fabricated into medical and surgical devices which are useful for a vast array of applications requiring complete absorption within the relatively short time periods set forth in the preceding sentence.

The biological properties of the bioabsorbable polymers of this invention used to form the device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

For purposes of defining the scope of this invention, the term "amino phenols" is meant to include 2-aminophenol, 3-aminophenol, 4-aminophenol, 2,3-diaminophenol, 2,4-diaminophenol and substituted equivalents of these compounds, as well as the dimers of these compounds.

For purposes of defining the scope of this invention, the term "amino benzoic acids" is meant to include 2-aminobenzoic acid, 3-aminobenzoic acid, 4-aminobenzoic acid, 2,3-diaminobenzoic acid, 2,4-diaminobenzoic acid, 2,5-diaminobenzoic acid, 3,5-diaminobenzoic acid and substituted equivalents of these compounds, as well as the dimers of these compounds.

For purposes of defining the scope of this invention, the term "amino salicylic acids" is meant to include 3-aminosalicylic acid, 4-aminosalicylic acid 5-aminosalicylic acid, and substituted equivalents of these compounds, as well as the dimers of these compounds.

For purposes of defining the scope of this invention the term "elastomer" is defined as a material which at room temperature can be stretched repeatedly to at least twice its original length and, upon immediate release of the stress, will return with force to its approximate original length. Preferably, the elastomer exhibits a high percent elongation and a low modulus, while possessing good tensile strength and good recovery characteristics. In the preferred embodiments of this invention, the elastomer from which the medical device or component of the device is formed exhibits a percent elongation greater than about 200, preferably greater than about 500. It will also exhibit a modulus (Young's Modulus) of less than about 40,000 psi, preferably less than about 20,000 psi. These properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch General description of the functionalization of the aromatic compound is selected from amine and/or carboxylic acid containing phenols, such as amino phenols, amino salicylic acids and amino benzoic acids is summarized below. Glycolic acid is used as a functionalization moiety for illustrative purposes.

Functionalization Moieties

Glycolic acid and lactic acid are also known as alpha hydroxy acids (AHA) present in fruits and other foods. These acids are helpful in treating a variety of skin ailments, such as dry skin, acne, and sunspots. These acids also improve skin texture and lessening fine facial wrinkles. Both glycolic and lactic acids also help loosening and removing dead skin cells. These acids are present in many healthiest foods we eat and drink, and they are considered to be safe when used correctly.

Glycolic acid occurs naturally as the chief acidic constituent of sugar cane juice and occurs in beet juice and unripe grapes. Its formula is HOCH$_2$COOH and is biodegradable. When glycolic acid is heated it readily loses water by self-esterification to form polyglycolic acid.

Glycolic acid can function as both an acid and an alcohol. This dual functionality leads to a variety of chemical reactions and valuable physical properties. Many surgical devices are made from polyglycolic acid. Studies of cosmetic applications have found that glycolic acid at low concentrations will diminish the appearance of fine lines on the skin.

The process of attaching a glycolic acid moiety to a phenolic compound is defined as glycolation and will be referred to as such in describing this invention:

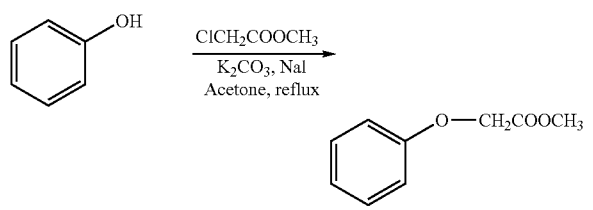

Lactic acid is a fermentation product of lactose. It is present in sour milk, koumiss, leban, yogurt, and cottage cheese. Lactic acid is produced in the muscles during intense activity. Calcium lactate, a soluble lactic acid salt, serves as a source of calcium in the diet. Lactic acid is produced commercially for use in foods and pharmaceuticals. Many surgical and orthopedic devices are made from polylactic acid. The esters of lactic acid are used as emulsifying agents in baking foods (stearoyl-2-lactylate, glyceryl lactostearate, glyceryl lactopalmitate).

The process of attaching a lactic acid moiety to a phenolic compound is defined as lactolation and will be referred to as such in describing this invention:

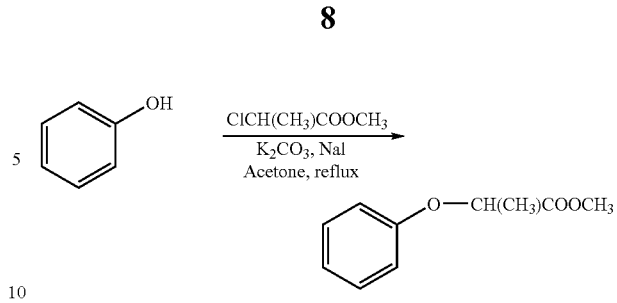

Epsilon-caprolactone is a cyclic monomer and is reactive, and the polymers derived are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers.

The process of attaching an open chain ε-caprolactone moiety to a phenolic compound is defined as caprolation and will be referred to as such in describing this invention:

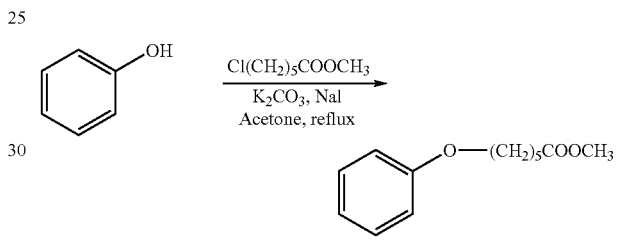

p-Dioxanone (1,4-dioxan-2-one) is a cyclic monomer and polymers are made via ring opening polymerization. Polyesters derived from this monomer are used in making absorbable surgical devices with longer absorption profile (slower hydrolysis) compared to polyglycolic acid. The absorbable surgical devices made from 1,4-dioxan-2-one are proved to be biologically safe, and biocompatible.

The process of attaching an open chain p-dioxanone moiety to a phenolic compound is defined as dioxonation and will be referred to as such in describing this invention:

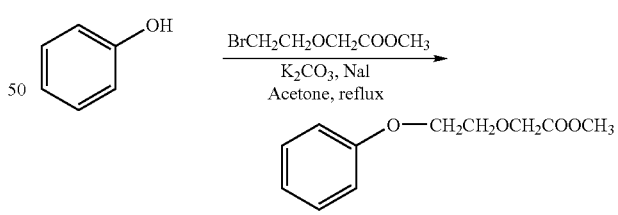

Many examples of both the phenolic amino acids and the functionalization moieties have been shown to be safe and biocompatible. The new functionalized phenolics can have controllable hydrolysis profiles, improved bioavailability, improved efficacy and enhanced functionality. The difunctional compounds can readily polymerize into biodegradable polyesters, polyester amides, polyurethanes, polydiamides, and polyanhydrides, for example, useful for many applications, including biomedical applications, foodstuffs, nutritional supplements, cosmetics, medicaments, coatings and others readily apparent to one skilled in the art.

An object of this invention is to combine these molecules, such as glycolic acid, lactic acid, p-dioxanone, ε-caprolactone, —(CH$_2$)$_y$COO—, where y is one of the integers 2,3,4 and between 6 and 24 inclusive, and —(CH$_2$CH$_2$O)$_z$CH$_2$COO—, where z is an integer between 2 and 24 inclusive, with phenolic amino acid, to form a new chemical entity. Preferred functionalization molecules are glycolic acid, lactic acid, p-dioxanone, and ε-caprolactone. Functionalization enhances the native value of the phenolic amino acid by releasing the phenolic amino acid moiety by hydrolysis or degradation of the compound. The compound degrades under controllable conditions in the environment, in the body of an animal, for example a mammalian, including a human.

The glycolic acid moiety, lactic acid moiety, dioxanone moiety, caprolactone moiety, moieties of —(CH$_2$)$_y$COO— where y is one of the numbers 2,3,4 and 6-24, and moieties of —(CH$_2$CH$_2$O)$_z$CH$_2$COO— where z is an integer between 2 and 24, including 2 and 24, have different hydrolysis or degradation rates and times over which they release the active phenolic amino acid moiety and thus do the functionalized phenolic acid made from them. The species used for functionalization supplies the release time or range dictated by the application. Glycolic acid based compounds hydrolyze faster than p-dioxanone based,, where as lactic acid and caprolactone based compounds take much longer to hydrolyze than glycolic acid and p-dioxanone based compounds. This desired time range may be obtained by using a combination of functionalized phenolic amino acids, that is, a blend of two or more functionalized compounds made from any two or more of the species glycolide, lactide, dioxanone and polydioxanone combined with one phenolic amino acid.

One aspect of the present invention combines the phenolic amino acid with one or more of the selected group of compounds to form a functionalized phenolic amino acid with uses in medicine, as enhanced drugs, drug intermediates, cancer preventing agents, nutrition supplements, nutriceuticals, antioxidants, controlled release preparations, cosmetic applications, flavors, coatings, drug intermediates, solvents for drugs, new monomers for polymerization, and when polymerized, as polymers for biomedical applications, drugs, nutrition supplements, nutriceuticals, drug delivery, cosmetic applications, flavors, and coatings.

The array of functionalized phenolic amino acids developed as an aspect of the invention, have a wide range of hydrolysis rates that are controllable. The specific moiety or combination of moieties used for functionalization yields a compound or mixture with specific hydrolysis ranges.

The new functionalized phenolic amino acids have more controllable hydrolysis profiles, improved bioavailability, improved efficacy and enhanced functionality. The difunctional compounds polymerize into biodegradable polymers, for example, useful for applications, including biomedical applications, foodstuffs, cosmetics, medicaments, coatings and other uses readily apparent to one skilled in the art.

The functionalized phenolics can be prepared according to any recognized method, but the Williamson ether synthesis method is the preferred method.

Williamson Synthesis

Preparation of ethers is an important reaction for which a wide variety of procedures have been developed during the last 100 years. The most commonly used method for the preparation of symmetrical and unsymmetrical ethers is the Williamson synthesis, involving a halide and an alkoxide. It is possible to mix the halide and alcohol with solid KOH and DMSO. The reaction involves an SN2 reaction in which an alkoxide ion replaces a halogen, sulfonyl or a sulfate group. Usually, alkyl halides are used. The alkoxide can be prepared by the reaction of the corresponding alcohol with an active metal such as metallic sodium or a metal hydride like NaH acting upon the alcohol. The resulting alkoxide salt is then reacted with the alkyl halide (sulfonate or sulfate) to produce the ether in an SN2 reaction.

Recently several new procedures for Williamson synthesis have developed in which the phase transfer catalysis (PTC) appear to very convenient and the reactions can be run under mild conditions with high yields. Most recently, it was reported that ethers could be prepared directly from alcohol and alkyl halides under microwave irradiation in the presence of a quaternary ammonium salt.

For the synthesis of aromatic ethers, the phenolic compound was reacted with one member of the group Na metal, NaH, and potassium carbonate to form a phenoxide and then reacted with an alkyl halide to form an aromatic ether as shown below:

The first step of the Williamson ether synthesis is the reaction of sodium hydride with a phenolic compound. Phenols are more acidic than alkanols because of resonance stabilization of the conjugated anion.

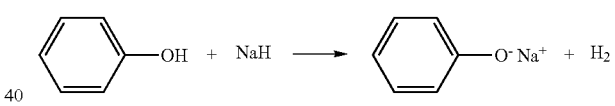

The resulting phenoxide ion is a powerful nucleophile, and reacts well with alkyl halide to form an ether.

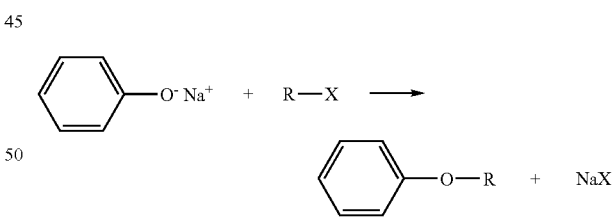

The alkyl halide must be primary so that the backside attack is not sterically hindered. When it is not primary, elimination usually results.

The general procedure for functionalizing phenolic compounds: To a mixture of phenolic compound, anhydrous potassium carbonate, sodium iodide and disodium phosphate in anhydrous acetone, while refluxing, the alkyl halide is added and refluxed for a period of from a few hours to several days until the reaction is essentially complete. Then the acetone is distilled off, water is added, and crude product is filtered and recrystallized from a solvent or mixture of solvents. Some times the products are purified by column chromatography. Solvent systems, reaction conditions, and purification methods are modified based on the phenol compound.

The process of preparing a phenolic ester with glycolic acid is shown below:

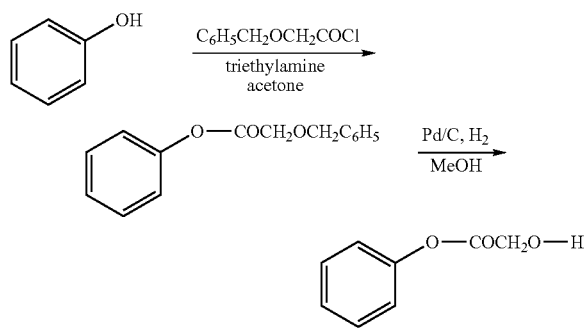

Benzyloxy acetyl chloride ($C_6H_5CH_2OCH_2COCl$) was prepared as described in the following reaction scheme:

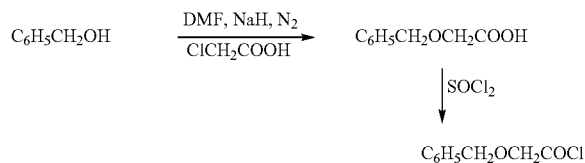

Using similar method, $C_6H_5CH_2OCH(CH_3)COCl$, $C_6H_5CH_2O(CH_2)_5COCl$, and $C_6H_5CH_2OCH_2CH_2OCH_2COCl$ were synthesized for preparation of phenolic esters of amino acids.

Lactic acid can function as both an acid and an alcohol. This dual functionality leads to a variety of chemical reactions and valuable physical properties. The process of preparing a phenolic ester with lactic acid is shown below:

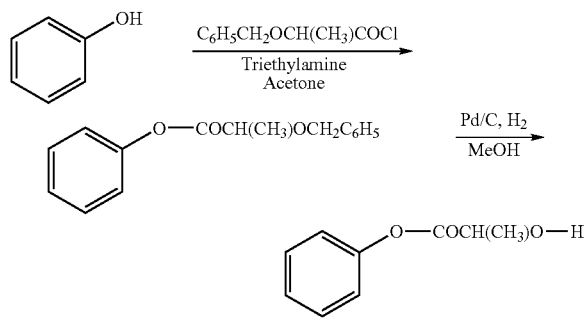

Epsilon-caprolactone can function as both an acid and an alcohol. This dual functionality leads to a variety of chemical reactions and valuable physical properties. The process of preparing a phenolic ester with epsilon-caprolactone is shown below:

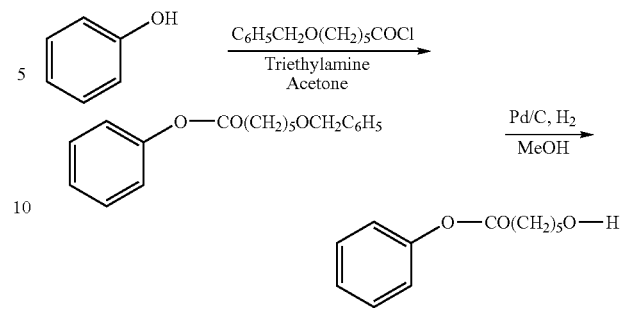

p-Dioxanone can function as both an acid and an alcohol. This dual functionality leads to a variety of chemical reactions and valuable physical properties. The process of preparing a phenolic ester with p-dioxanone is shown below:

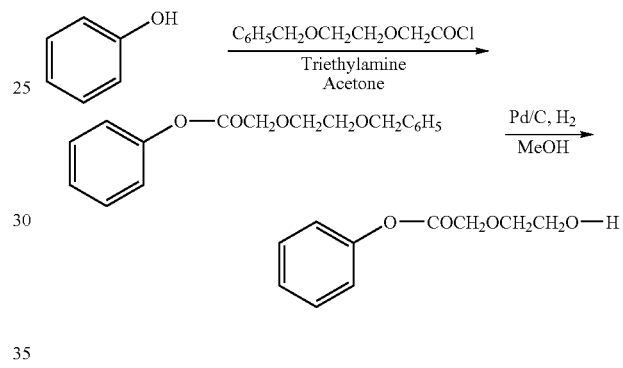

The phenolic amino acids and the functionalization moieties of the present invention are safe and biocompatible. The new functionalized phenolic amino acids have controllable hydrolysis profiles, increased solubility, improved bioavailability, improved efficacy and enhanced functionality. The difunctional compounds readily polymerize into biodegradable polyesters, polyester amides and polyurethanes, for example, useful for many applications, including biomedical applications, foodstuffs, nutritional supplements, cosmetics, biodegradable chewing gums, flavors, medicaments, coatings and others readily apparent to one skilled in the art.

One aspect of this invention is to combine one or more of these moieties, such as glycolic acid, lactic acid, p-dioxanone, ε-caprolactone, —$CO(CH_2)_mO$—, where m is one of the integers 2,3,4 and between 6 and 24 inclusive, and —$COCH_2O(CH_2CH_2O)_n$— where n is an integer between 2 and 24, with phenolic compounds, to form a new chemical entity through an esterification process. Preferential examples of functionalization molecules are glycolic acid, lactic acid, p-dioxanone, and ε-caprolactone. Functionalization enhances the native value of the phenolic compound while improving its solubility by forming a compound which will controllably release the phenolic moiety into the environment or into the body of a mammalian, preferably a human.

The glycolic ester moiety, lactic ester moiety, dioxanone ester moiety, caprolactone ester moiety, moieties of —$CO(CH_2)_mO$—, where m is one of the integers 2,3,4 and between 6 and 24 inclusive, and —$COCH_2O(CH_2CH_2O)_n$— where n is an integer between 2 and 24, have different hydrolysis or degradation rates and times over which they release the active phenolic moiety and thus do the functionalized phenolic compounds made from them. The species used for functionalization supplies the release time or range dictated by the application. Glycolic acid based compounds hydrolyze faster than p-dioxanone based, where as lactic acid and caprolactone based compounds take much longer to hydrolyze than glycolic acid and p-dioxanone based compounds. This desired time range may be obtained by using a combination of functionalized phenolic compounds, that is, a blend of two or more functionalized compounds made from any two or more of the species glycolide, lactide, dioxanone and polydioxanone combined with one phenolic compound.

The present invention also combines the phenolic amino acid with one or more of the ester-forming functionalizing group of compounds to form a functionalized phenolic with uses in medicine, as enhanced drugs, drug intermediates, cancer preventing agents, nutrition supplements, nutriceuticals, antioxidants, controlled release preparations, cosmetic applications, biodegradable chewing gums, flavors, coatings, drug intermediates, solvents for drugs, new monomers for polymerization, and when polymerized, as polymers for biomedical applications, drugs, nutrition supplements, nutriceuticals, drug delivery, cosmetic applications, flavors, and coatings.

The array of functionalized phenolic compounds developed as an aspect of the invention, have a wide range of hydrolysis rates that are controllable. The specific moiety or combination of moieties used for functionalization yield a compound or mixture with specific, controllable hydrolysis ranges.

The new functionalized phenolic amino acids have more highly controllable hydrolysis profiles, increased solubility, improved bioavailability, improved efficacy and enhanced functionality. They can be targeted to release the active phenolic component in specific organs or body parts. The difunctional compounds polymerize into biodegradeable polymers, for example, useful for biomedical applications, foodstuffs, biodegradable chewing gums, implantable medical devices, cosmetics, medicaments, coatings and other uses readily apparent to one skilled in the art.

Synthesis of Phenolic Amides:

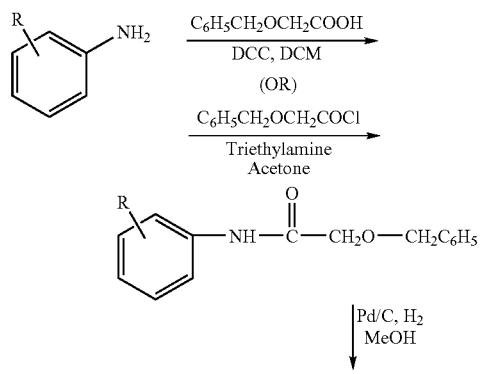

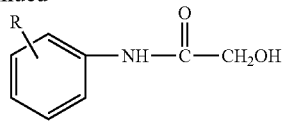

Benzyloxyamides are prepared by reacting benzyloxy acetic acid with an amine using dicyclohexylcarbodiimide (DCC) as coupling agent, in dichloromethane (DCM) as a solvent. The amine is dissolved in DCM and benzyloxyacetic acid is added. While maintaining below room temperature, DCC solution in DCM is added dropwise. The reaction generally proceeds cleanly for the formation of an amide. The urea formed is not soluble in DCM, and the urea can be filtered off to get the amide. In a second method the amines are reacted with the acid chloride directly using a base, such as $K_2CO_3$, $NaHCO_3$ or triethyl amine to neutralize the HCl that is formed during the reaction. Acetone is a good solvent for this reaction. Both methods are suitable for preparing benzyloxyamides.

Synthesis of Phenolic Esters:

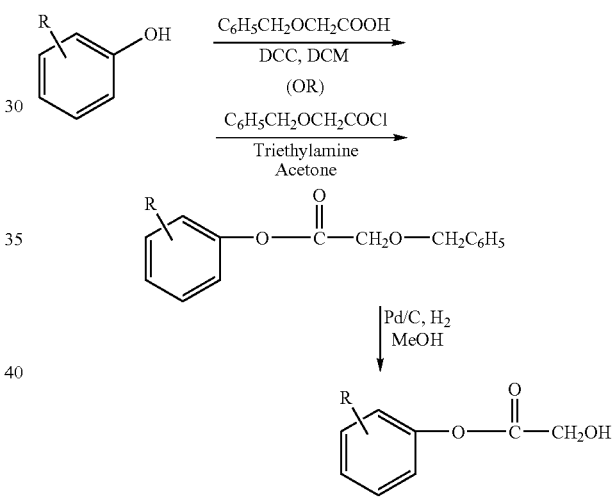

We can use similar conditions as above for preparing benzyloxyesters.

Debenzylation

Debenzylations were done using 50% wet Pd/C (5%) with hydrogen pressure up to 4 kg. MeOH or DMF can be as solvents. Dry Pd/C(5%) can be also used to avoid ester hydrolysis. DMF, MeOH, or Ethyl acetate can be used for this reaction.

The foregoing synthetic methods can be used to prepare the following monomers, and an absorbable polymer prepared therefrom:

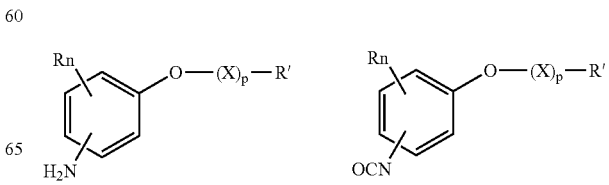

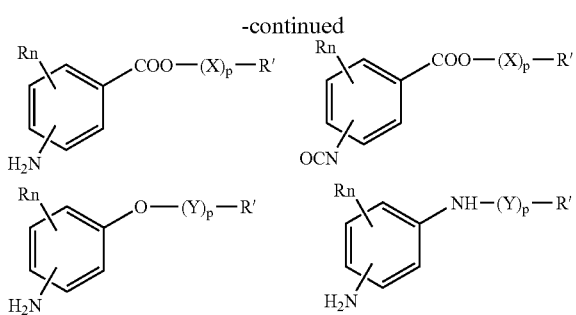

Wherein each X represents a member independently selected from:
—CH$_2$COO— (glycolic acid moiety),
—CH(CH$_3$)COO— (lactic acid moiety),
—CH$_2$CH$_2$OCH$_2$COO— (dioxanone moiety),
—CH$_2$CH$_2$CH$_2$CH$_2$CH$_2$COO— (caprolactone moiety),
—(CH$_2$)$_y$COO— where y is one of the numbers 2,3,4 or 6-24 inclusive, and
—(CH$_2$CH$_2$O)$_{z'}$CH$_2$COO— where z' is an integer between 2 and 24, inclusive;

each Y represents a member independently selected from:
—COCH$_2$O— (glycolic ester moiety),
—COCH(CH$_3$)O— (lactic ester moiety),
—COCH$_2$OCH$_2$CH$_2$O— (dioxanone ester moiety),
—COCH$_2$CH$_2$CH$_2$CH$_2$CH$_2$O— (caprolactone ester moiety),
—CO(CH$_2$)$_m$O— where m is an integer between 2-4 and 6-24 inclusive,
—CO CH$_2$O(CH$_2$CH$_2$O)$_n$— where n is an integer between 2 and 24, inclusive;

R' is hydrogen, benzyl or an alkyl group, the alkyl group being either straight-chained or branched; p is an integer between 1 and 4, inclusive; and Rn represents one or more members selected from H, alkoxy, benzyloxy, aldehyde, halogen, carboxylic acid —NO$_2$, which is attached directly to an aromatic ring or attached through an aliphatic chain.

Many species of both the aminophenolics and the functionalization moieties have been shown to be safe and biocompatible. The new functionalized aminophenolic compounds have controllable hydrolysis profiles, increased solubility, improved bioavailability, improved efficacy and enhanced functionality. The difunctional compounds can readily polymerize into biodegradable polyamides, polyester-urethanes, polyester amides and polyurethanes, for example, useful for many applications, including biomedical applications, such as stents, stent coatings, drug delivery, and surgical devices and others readily apparent to one skilled in the art.

One aspect of this invention is to combine one or more of these moieties, such as glycolic acid, lactic acid, p-dioxanone, ε-caprolactone, —CO(CH$_2$)$_m$O—, where m is one of the integers 2,3,4 and between 6 and 24 inclusive, and —COCH$_2$O(CH$_2$CH$_2$O)$_n$— where n is an integer between 2 and 24, with phenolic compounds, to form a new chemical entity through an esterification process. Preferred functionalization molecules are glycolic acid, lactic acid, p-dioxanone, and ε-caprolactone. Functionalization enhances the native value of the phenolic compound while improving by its solubility by forming a compound which will controllably release the phenolic moiety into the environment or into the body of a mammalian, preferably a human.

The glycolic ester moiety, lactic ester moiety, dioxanone ester moiety, caprolactone ester moiety, moieties of —CO(CH$_2$)$_m$O—, where m is one of the integers 2,3,4 and between 6 and 24 inclusive, and —CO CH$_2$O (CH$_2$CH$_2$O)$_n$— where n is an integer between 2 and 24, have different hydrolysis or degradation rates and times over which they release the active phenolic moiety and thus do the functionalized phenolic compounds made from them. The species used for functionalization supplies the release time or range dictated by the application. Glycolic acid based compounds hydrolyze faster than p-dioxanone based, where as lactic acid and caprolactone based compounds take much longer to hydrolyze than glycolic acid and p-dioxanone based compounds. This desired time range may be obtained by using a combination of functionalized phenolic compounds, that is, a blend of two or more functionalized compounds made from any two or more of the species glycolide, lactide, dioxanone and polydioxanone combined with one phenolic compound.

The array of functionalized aminophenolic compounds developed as an aspect of the invention, have a wide range of hydrolysis rates that are controllable. The specific moiety or combination of moieties used for functionalization yield a compound or mixture with specific, controllable hydrolysis ranges.

These new functionalized aminophenolic compounds have more highly controllable hydrolysis profiles, increased solubility, improved bioavailability, improved efficacy and enhanced functionality. They can be targeted to release the active aminophenolic component in specific organs or parts of the body. The difunctional compounds polymerize into biodegradable polymers, for example, useful for applications, including biomedical applications, such as stents, stent coatings, drug delivery, and surgical devices and others readily apparent to one skilled in the art.

Processes for preparing polymers of the invention are provided as further embodiments of the invention and are illustrated by the following procedures, as a simplified illustration:

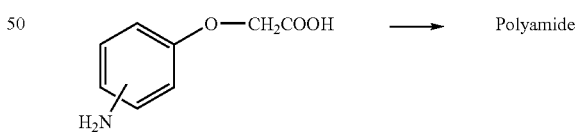

Polyamides can be prepared by self condensation or by reacting with an amino acid(HOOC—R—NH$_2$)

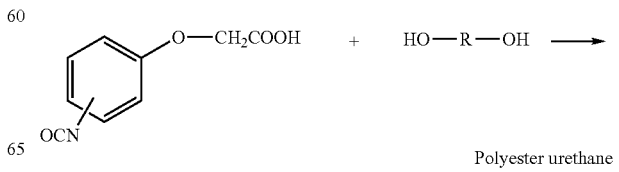

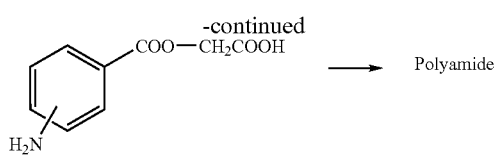

Polyamides can be prepared by self condensation or by reacting with an amino acid (HOOC—R—NH$_2$)

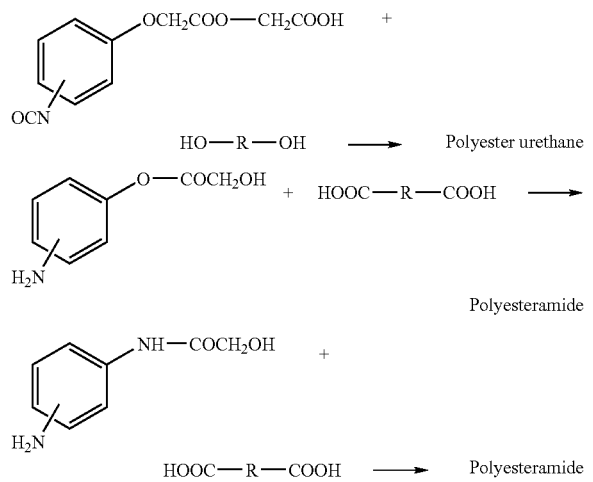

The monomer compounds of the invention can be used to polymerize biocompatible, biodegradable polyurethanes, polyesterurethanes, and polyamides useful in a variety of applications where delivery of a biologically active compound is desired. Examples of such applications include, but are not limited to, medical, dental and cosmetic uses.

In another embodiment, copolymers of the absorbable polymers of this invention can be prepared by preparing a prepolymer under melt polycondensation conditions, then adding at least one lactone monomer or lactone prepolymer. The mixture would then be subjected to the desired conditions of temperature and time to copolymerize the prepolymer with the lactone monomers.

The polymers of the invention are prepared in accordance with methods commonly employed in the field of synthetic polymers to produce a variety of useful products with valuable physical and chemical properties. The polymers are readily processed into pastes or solvent cast to yield films, coatings, microspheres and fibers with different geometric shapes for design of various medical implants, and may also be processed by compression molding and extrusion.

Polyurethanes, polyester urethanes, and polyamides prepared in accordance with the present invention have average molecular weights of about 1500 to about 100,000 calculated by Gel Permeation Chromatography (GPC) relative to narrow molecular weight polystyrene standards. Preferred Polyurethanes, polyester urethanes, and polyamides have average molecular weights of about 1500 up to about 100,000 calculated by Gel Permeation Chromatography (GPC) relative to narrow molecular weight polystyrene standards. Preferred Polyurethanes, polyester urethanes, and polyamides have average molecular weights of about 1500 up to about 40,000.

Medical implant applications include the use of polyurethanes, polyester urethanes, and polyamides to form shaped articles such as vascular grafts and stents, bone plates, sutures, implantable sensors, implantable drug delivery devices, stents for tissue regeneration, and other articles that decompose into non-toxic components within a known time period.

In more detail, the surgical and medical uses of the filaments, films, and molded articles of the present invention include, but are not necessarily limited to:

Knitted products, woven or non-woven, and molded products including:
a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. suture knot clip
j. orthopedic pins, clamps, screws, and plates
k. clips (e.g., for vena cava)
l. staples
m. hooks, buttons, and snaps
n. bone substitutes (e.g., mandible prosthesis)
o. intrauterine devices (e.g., spermicidal devices)
p. draining or testing tubes or capillaries
q. surgical instruments
r. vascular implants or supports
s. vertebral discs
t. extracorporeal tubing for kidney and heart-lung machines
u. artificial skin and others In another embodiment, the polymer of this invention is used to coat a surface of a surgical article to enhance lubricity of the coated surface. The polymer may be applied as a coating using conventional techniques. For example, the polymer may be solubilized in dilute solution of volatile organic solvent, e.g. acetone, methanol, ethyl acetate or toluene, and the article immersed in the solution to coat its surface. Once the surface is coated, the surgical article is removed from the solution where it can be dried at an elevated temperature until solvent and any residual reactants are removed.

Although it is contemplated that numerous surgical articles (including but not limited to endoscopic instruments) can be coated with the polymer of this invention to improve the surface properties of the article, the preferred surgical articles are surgical sutures, stents and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, .epsilon.-caprolactone, 1,4-dioxanone, and trimethylene carbonate. The preferred suture is a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 percent by weight. If the amount of coating on the suture were greater than about 30 weight percent, then it may increase the risk that the coating may flake off when the suture is passed through tissue Sutures coated with the polymers of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of this invention.

In another embodiment of the present invention when the article is a metal stent, the amount of coating applied to the surface of the article is an amount which creates a layer with a thickness ranging preferably between about 2 to about 20 microns on the stent, more preferably about 4 to about 8 microns. If the amount of coating on the stent were such that the thickness of the coating layer was greater than about 20 microns, or if the thickness was less than about 2 microns, then the desired performance of the stent as it is passed through tissue may not be achieved.

In another embodiment of the present invention when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

Polymers of the present invention can also be incorporated into oral formulations and into products such as skin moisturizers, cleansers, pads, plasters, lotions, creams, gels, ointments, solutions, shampoos, tanning products and lipsticks for topical application.

Another aspect of the present invention provides absorbable polyamides prepared from at least one compound of the formula:

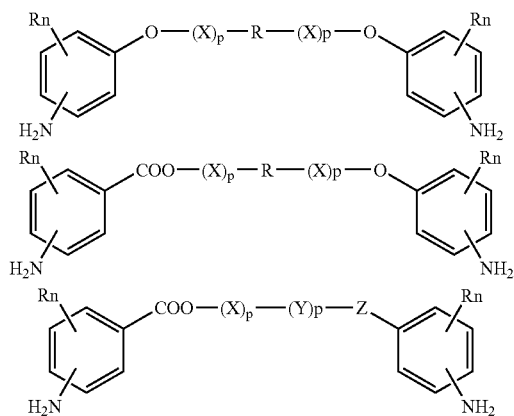

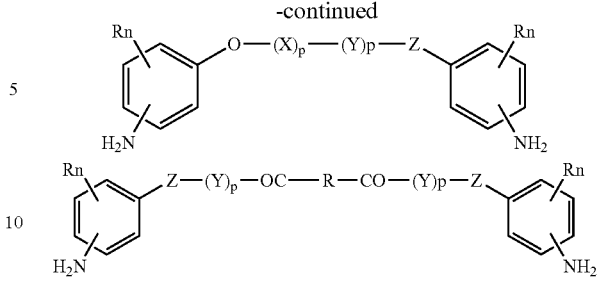

Wherein each X represents a member independently selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is one of the numbers 2,3,4 and 6-24 inclusive; and
—$(CH_2CH_2O)_{z'}CH_2COO$— where z' is an integer between 2 and 24, inclusive;

each Y represents a member independently selected from:
—$COCH_2O$— (glycolic ester moiety);
—$COCH(CH_3)O$— (lactic ester moiety);
—$COCH_2OCH_2CH_2O$— (dioxanone ester moiety);
—$COCH_2CH_2CH_2CH_2O$— (caprolactone ester moiety);
—$CO(CH_2)_mO$— where m is an integer between 2-4 and 6-24 inclusive; and
—$COCH_2O(CH_2CH_2O)_n$— where n is an integer between 2 and 24, inclusive;

R' is hydrogen, benzyl or an alkyl group, the alkyl group being either straight-chained or branched; p is an integer between 1 and 4, inclusive; and Rn represents one or more members selected from H, alkoxy, benzyloxy, aldehyde, halogen, carboxylic acid and —$NO_2$, which is attached directly to an aromatic ring or attached through an aliphatic chain.

The aromatic compound is selected from amine and/or carboxylic acid containing phenols, such as amino phenols, amino salicylic acids and amino benzoic acids.

Processes for preparing polyamides of the invention are provided as further embodiments of the invention and are illustrated by the following procedures, as a simplified illustration:

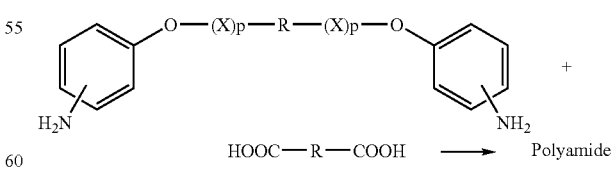

The diamines can be reacted with diisocyantes (OCN-R—NCO) to prepare bidegradable poluureas.

Another aspect of the present invention provides an absorbable polyurethane prepared from at least one compound of the formula:

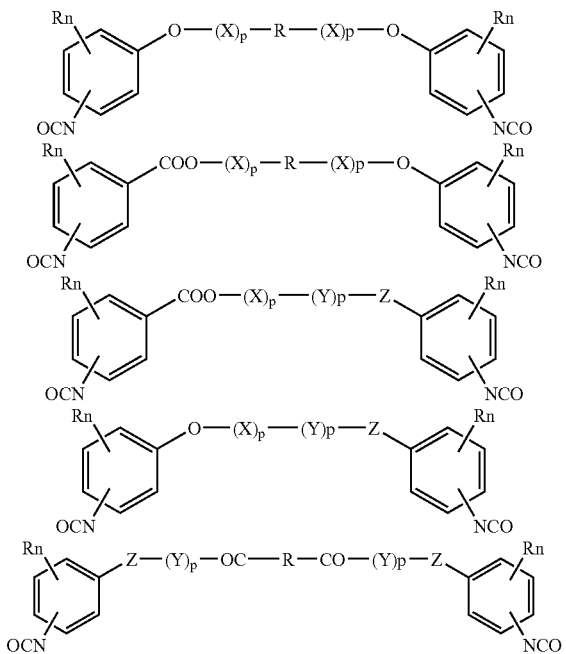

Wherein each X represents a member independently selected from:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is one of the numbers 2,3,4 and 6-24 inclusive; and
—(CH$_2$CH$_2$O)$_{z'}$CH$_2$COO— where z' is an integer between 2 and 24, inclusive;

each Y represents a member independently selected from:
—COCH$_2$O— (glycolic ester moiety);
—COCH(CH$_3$)O— (lactic ester moiety);
—COCH$_2$OCH$_2$ CH$_2$O— (dioxanone ester moiety);
—COCH$_2$CH$_2$CH$_2$CH$_2$CH$_2$O—(caprolactone ester moiety);
—CO(CH$_2$)$_m$O— where m is an integer between 2-4 and 6-24 inclusive; and
—CO CH$_2$O(CH$_2$CH$_2$O)$_n$— where n is an integer between 2 and 24, inclusive;

each R' is hydrogen, benzyl or an alkyl group, the alkyl group being either straight-chained or branched; each p is independently an integer between 1 and 4, inclusive, Z is O or NH; and Rn represents one or more members selected from H, alkoxy, benzyloxy, aldehyde, halogen, carboxylic acid and —NO$_2$, which is attached directly to an aromatic ring or attached through an aliphatic chain.

The aromatic compound is selected from amine and/or carboxylic acid containing phenols, such as amino phenols, amino salicylic acids and amino benzoic acids.

A further object of the present invention is to provide novel safe, biocompatible and bioabsorbable diisocyanate-based adhesives and in particular metabolically-acceptable surgical adhesives. It is also an object to provide safe, bicompatible surgical adhesives which are biodegradable. It would also be desirable to provide a method for closing wounds in living tissue by use of novel, metabolically-acceptable surgical adhesives that are low in toxicity as a consequence of their physical properties.

It is a further object of the present invention to provide novel polyurethanes which are biodegradable and biocompatible.

It is a further object of the present invention to provide novel polyurethanes of the segmented variety which are bioabsorbable.

It is a further object of the present invention to provide a chain extender for use in the formation of biodegradable polyurethanes.

Processes for preparing polyurethanes of the invention are provided as further embodiments of the invention and are illustrated by the following procedures, as a simplified illustration:

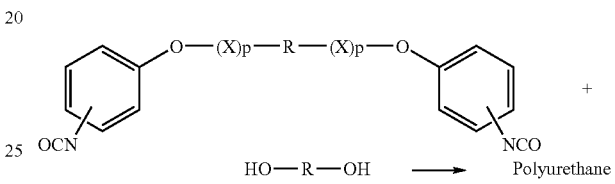

These isocyanates can be reacted with diamines (H$_2$N—R—NH$_2$) to prepare biodegradable polyureas Chain Extenders: the nature of the chain extender group "R" in a polymer of the invention is not very critical provided the polymer of the invention possesses acceptable mechanical properties and release kinetics for the selected therapeutic application. The chain extender group R is typically a divalent organic radical having a molecular weight of from about 60 to about 5000. More preferably, R has a molecular weight of from about 100 to about 1000.

The chain extender group may be biologically inactive, or may itself possess biological activity. The chain extender group can also be a polyethylene oxide. The chain extender group can also be polyesters derived from at least one lactone monomer, such as glycolide, lactide, p-dioxanone, trimethylenecarbonate, and caprolactone. The chain extender group can also comprise other functional groups (including hydroxy groups, amine groups, carboxylic acids, as well as others) that can be used to modify the properties of the polymer (e.g. for branching, for cross linking).

The mechanical properties, such as ultimate tensile strength, of polyurethanes made according to the present invention may in some cases be influenced primarily by the polyol as opposed to the hard segment as in typical segmented polyurethanes.

Suitable diols or polyols for use in the present invention are diol or diol repeating units with up to 8 carbon atoms. Examples of suitable diols include diols selected from 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from polyethylene glycol and polypropylene glycol with molecular weights of 500-10000.

Preferably, the polyurethane is of the type known as segmented polyurethane, which is characterized by a formation of repeating soft and hard blocks formed from such things as a polyol, a diisocyanate and a chain extender and can occur in a linear, branched or networked form. The term chain extender is intended to refer to a multi-functional molecule which may be reacted with the previously synthesized prepolymer to generate a high molecular weight polyurethane for example. However, the formation of polyurethane may also be carried out using such processes as a single step process involving reaction of the chain extender with the diisocyanate and the polyol which do not involve the formation of a prepolymer.

Preferably, the polyol is selected according to toxicity when broken down or otherwise liberated. Two examples of appropriate polyols are polyethylene oxide and polycaprolactone diol. Others, which may be suitable in some cases. The constituents making up the polyurethane may be selected so as to be biodegradeable to substantially nontoxic constituents. The term 'substantially non-toxic' is intended to refer to materials which when present in the body are physically tolerable and, more specifically, do not cause appreciable cell death (cytotoxicity) or detrimental alteration of normal cell function (such as mutagenic response). This would of course depend on the area of application. For example, detailed in vivo tests may be appropriate to determine the effect of the material on the neighboring cells.

Depending on the formation route selected, these cleavable sites may be regular along the length of the chain extender, thereby giving the segmented polyurethane a biodegradeability which is, by some measure, predictable. Biodegradability is influenced by a number of factors, including crystallinity.

The hydrophilicity of the polymer may also influence the degradability, that is, the extent to which water is accessible to the polymer matrix. In those cases where the chain extender has enzyme recognizable side groups, the access of the water to the surface of the matrix should increase the rate at which the enzyme can catalyze the reaction between water and the hydrolyzable cleavage sites.

The number of cleavage sites also influence biodegradability. The higher the number of sites generally, the greater the rate of degradation. Preferably, the cleavable site is an ester site and, more preferably, the cleavable ester site is adjacent one or more amino acids. This provides segmented polyurethanes with cleavable sites in its chain extender that may be arranged to be recognizable by enzymes.

In one embodiment, the diisocyanate is reacted with the soft segment polyol, in suitable conditions to form a prepolymer; and the prepolymer is then reacted with the chain extender, again in suitable conditions, to form the polyurethane.

Alternatively, multi-functional components could be employed to produce a cross-linked network, and hence nonlinear, segmented polyurethane. This for example, could be achieved by the use of a branched complex bearing more than two hydroxyl groups, such as for example a triol. In another case, certain amino acids may also contribute to the formation of a networked polymer. Lysine for example, having an amine group on its side chain, may be reacted with such sites as a isocyanate group on the diisocyanate. Additionally, several lysines may be present in the amino acid group thereby providing potential bonding sites between each corresponding amine and another site such as an isocyanate group. Thus, such multi-functional components allow for the formation of nonlinear segmented polyurethane.

Thus, in one embodiment, substantially non-toxic degradable polyurethane can be formed from amino acids and substantially non-toxic diols, in such a manner to be useful as biomaterials for a variety of applications such as artificial skin, wound dressings, tissue engineering scaffolds and the like. The polyurethane materials may be formed by melt and solvent processing techniques such as dissolving the polymer into a solvent, pouring the mixture onto a flat sheet or into a mold and evaporating the solvent, with the polymer remaining therein. Other melt processing techniques may be available by melting a blank of polyurethane and manipulating it into a shape as desired, including tubes and fibers. A porous polyurethane may be formed in a number of ways, including the addition of a gas (typically carbon dioxide) into the polymerization reaction, trapping the gas into the polymer structure. Alternatively, salt crystals can be added to the solvent polymer mixture during casting wherein the salt is not dissolved. The mixture may be deposited into a dish causing the solvent to evaporate, with the salt material being removed by washing with water.

The polyurethane material formed herein may be used in a number of different forms and in a range of applications, both in the biomedical field and others. The material may be fabricated by casting or other molding techniques to form a substrate, which can be used along or combined with other substrates to form homogenous multi-layered materials. Such multilayered homogeneous polyurethane materials may be formed with layers having different degrees of degradability. Such substrates may range in thickness from about 1 micron to about 5 millimeters for applications suitable for skin repair and the like and perhaps more particularly from about 10 microns to 3.5 millimeters, and still perhaps more particularly from about 50 microns to about 2 millimeters. The thinner the substrate, the more care is needed in handling.

In the case of bone regeneration and the like, the polyurethane material may range in thickness from about 1 cm to about 5 cm or higher, depending on the specific application, including the dimensions of the bone being regenerated. Alternatively, the layered polyurethane material may be combined with other naturally occurring materials such as plant materials or biological materials such as prepared animal tissue (in a cellularized form or otherwise), cell layers and the like. The layered polyurethane material may also be combined with other non-naturally occurring materials such as other polymer layers, fabric layers and the like.

Such uni- and multi-layered materials utilizing the polyurethane materials described herein may have a number of useful applications in the biomedical field, such as to function as a tissue scaffolding material, a wound dressing or the like.

The polyurethane material may also be formed as an impermeable film or bulk material or in a porous form and may be a suitable site to establish a cell layer, for example to be used in the seeding of regenerative tissue layers, in such cases as in the healing of skin wounds and the like.

The polyurethane material is believed to be especially useful for use as a tissue engineering scaffold which is a structure for the growth or regeneration of tissue. The polyurethane lends itself to such uses since the enzyme catalyzed degradation may in some cases work concurrently with the migration or growth of cells into the material, while desirably degrading in the process into its substantially non-toxic constituents. For example, testing of polyurethane made according to the present invention, has indicated significant surface modification in the presence of an enzyme in solution, and which is believed to be caused by enzyme catalyzed cleavage, gradually opening the matrix to cell migration as a result. It is also possible, in some cases, that cells migrating into or located adjacent the matrix, may themselves exude proteolytic enzymes which will likewise mediate further hydrolytic cleavage.

Such tissue engineering scaffolds may have applications in the regeneration of skin and other organs, bone, cartilage, ligaments, tendons, bladder and other tissue. The polyurethane material may also be useful in the production of sutures, which require good mechanical strength, and drug release matrices, in view of their need for non-toxic degradability. The polyurethane material may also be useful for other non-biomedical applications, where degradability into substantially non-toxic constituents is an asset. The polyurethane material lends itself to sterilization by such techniques as gamma radiation and ethylene oxide treatments.

In another embodiment of the present invention, the inventive polymers can be used as a pharmaceutical carrier in a drug delivery matrix. The matrix is formed by mixing the polymer with a therapeutic agent. A vast variety of different therapeutic agents can be used in conjunction with the polymers of the invention. In general, therapeutic agents administered via the pharmaceutical compositions of the invention include, without limitation: antiinfectives such as antibiotics and antiviral agents; analgesics and analgesic combinations; anorexics; antihelmintics; antiarthritics; anti-asthmatic agents; anticonvulsants; antidepressants; antidiuretic agents; antidiarrheals; antihistamines; antiinflammatory agents; antimigraine preparations; antinauseants; antineo-plastics; anti-parkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immuno-suppressives; muscle relaxants; para-sympatyholytics; psychostimulants; sedatives; and tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention may be formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agent or compound, however, if water is to be used it should be added immediately before administration.

The amount of therapeutic agent will be dependent upon the particular drug employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on release profile desired and the amount of drug employed. The product may contain blends of polymers of this invention to provide the desired release profile or consistency to a given formulation.

The polymers of this invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over, one to 2,000 hours, preferably two to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and polymers of this invention may be tested in appropriate in vitro and in vivo models to achieve the desired drug release profiles. For example, a drug could be formulated with a polymer of this invention and orally administered to an animal. The drug release profile is monitored by appropriate means such as, by taking blood samples at specific times and assaying the samples for drug concentration. Following this or similar procedures, those skilled in the art are able to formulate a variety of formulations.

Embodiments of the present invention will be described with reference to the following Examples, which are presented for illustrative purposes only and are not intended to limit the scope of the invention. Melting points were measured for all products by using a Polmon (MP 96) melting point apparatus. For all the products, NMR was run using a Varian 200 MHz and tetramethylsilane as an internal standard.

EXAMPLE 1

(4-Acetylamino-phenoxy)-acetic acid ethyl ester (1)

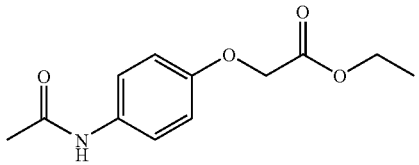

Ethyl bromoacetate (452 g, 2.7 mol.) was added to a mixture of paracetamol (300 g, 1.984 mol) and anhydrous $K_2CO_3$ (1.80 kg, 7.814 mmol) in anhydrous acetone (3 L) and refluxed for 16 hours. Acetone was distilled and water (5 L) was added. Crude 1 was filtered, dried and recrystallised from a mixture of toluene:hexane (1:5) to give pure 1 (377 grams, 80%) as a white shining powder. The melting point was found to be 104.2-106.2° C.

EXAMPLE 2

(4-Amino-phenoxy)acetic acid HCl (2)

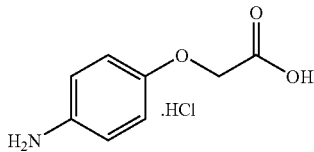

(4-Acetylamino-phenoxy)-acetic acid ethyl ester 1 (375 grams, 1.582 mmol), in concentrated Hydrochloric acid (9.36 liters) was refluxed for 12 Hours. Excess concentrated Hydrochloric acid was distilled off in vacuum and filtered hot. The mixture was cooled to 10° C., filtered and dried to give pure 2(250 g, 77.6%) as a wheat colored powder.

M.p: 224-226° C.; $^1$HNMR ($D_2O$) δ 4.68 (s, 2H, OCH2), 3.65 (s, 3H, ester), 7.0 (d, 2H, Ar), 7.30 (d, 2H, Ar)

EXAMPLE 3

(4-Amino-phenoxy)-acetic acid methyl ester (3)

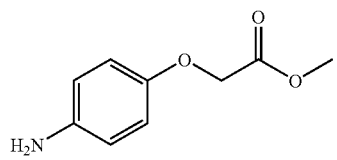

Method A

Through a mixture of (4-Amino-phenoxy) acetic acid HCl 2 (250 g, 1.228 mol) in methanol (5 liters) was passed dry HCl gas at 10° C. for one hour and refluxed for ten hours. Methanol (3.5 liters) was distilled off and ice water (1 liter) was added and the pH was adjusted to 7.5 with $K_2CO_3$. Crude 3 was filtered, dried and recrystallized from a mixture of chloroform:hexane (1:5) to give pure 3 (130 g, 58.5%) as a light brown powder Method B Methyl (4-nitrophenoxy) acetate 7 (30 grams, 142.18 mol) was dissolved in methanol (150 ml) in a pressure vessel. Raney nickel (20 g) was added and the mixture stirred under atmosphere of hydrogen (4 kg) for 8 hours. Catalyst was removed by filtration and methanol distilled off under vacuum. Crude 3 was purified by column chromatography on silica gel using chloroform as eluant to get pure 3 (22 grams, 85.5%) as a light brown powder.

M.p: 65-66.8° C.; $^1$HNMR ($CDCl_3$) δ 3.04 (bs, 2H, NH2), 3.78 (s, 3H, ester), 4.54 (s, 2H, CH2), 6.58 (d, 2H, Ar), 6.72 (d, 2H, Ar)

EXAMPLE 4

(4-Isocyanato-phenoxy)-acetic acid methyl ester (4)

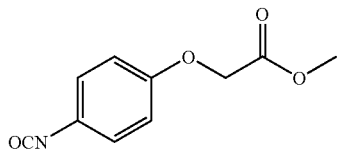

To a mixture of (4-aminophenoxy)-acetic acid methyl ester 3 (15 g, 82.87 mmol) and triethylamine (16.77 g, 165.73 mmol) in toluene (225 ml) under nitrogen atmosphere at 0° C. was added triphosgene (9 g, 30.33 mmol) in one lot. The reaction was exo-thermic and the temperature rose to 25° C. Later the reaction mixture was heated to 75° C. over a period of one hour and maintained at this temperature for 26 hours. The reaction mixture was cooled to room temperature, the solids were filtered off, and toluene was distilled off under vacuum to get crude 4, which was vacuum distilled to get pure 4 (10 grams, 58.3%) as a white powder with an m.p between 50-53° C.

EXAMPLE-5

[4-(2-Hydroxy-ethoxycarbonylamino)-phenoxy]-acetic acid methyl ester (5)

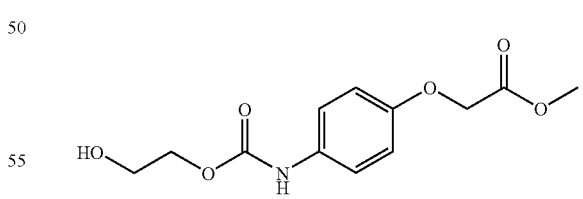

(4-Isocyanatophenoxy)-acetic acid methyl ester 4 (15 g, 72.46 mmol) was added to ethylene glycol (30 ml) at room temperature. The reaction was exothermic and the temperature rose to 42° C. Later the reaction mixture was stirred at room temperature for 16 hours. Water (100 ml) was added and crude 5 was filtered, dried and purified by column chromatography on silica gel using chloroform as eluant to get pure 5 (16.17 g, 82.9%) as an off-white powder with an m.p between 85.5-87.5° C.

EXAMPLE-6

{4-[2-(4-Methoxycarbonylmethoxy-phenylcarbamoyloxy)-ethoxycarbonylamino]-phenoxy}-acetic acid methyl ester (6)

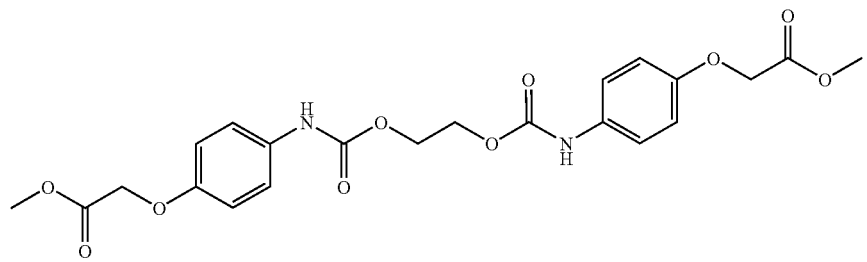

To [4-(2-Hydroxyethoxycarbonylamino)-phenoxy]-acetic acid methyl ester 5 (1 g, 3.72 mmol) in toluene (10 ml) was added (4-Isocyanatophenoxy)-acetic acid methyl ester 4 (0.8 gram, 3.8 mmol) at room temperature and heated to 50° C. for 20 hours. Toluene was distilled off and water (10 ml) was added. Crude 6 was extracted into chloroform, dried over sodium sulphate, distilled and purified by column chromatography on silica gel using chloroform as eluant to g pure 6 (1 gram, 56.5%) as a white fluffy powder.

EXAMPLE 7

Methyl (4—Nitro phenoxy) acetate (7)

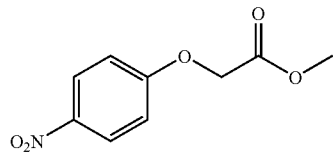

To a mixture of 4-nitrophenol (100 g, 719 mmol) and anhydrous $K_2CO_3$ (400 gm, 2.894 mol) in anhydrous acetone (950 ml) was added methyl chloroacetate (114 g, 1.050 moles) and refluxed for 12 hours. Acetone was distilled off and water (1500 ml) was added. Crude 7 was filtered, dried and recrystallised from a mixture of ethyl acetate:hexane (1:5) to give pure 7 (110 g, 72.5%) as a white fluffy powder with an m.p between 97-98.4° C.

EXAMPLE 8

2-(4-Acetylamino-phenoxy)-propionic acid methyl ester (8)

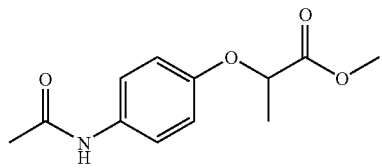

To a mixture of paracetamol (150 g, 992 mmol), anhydrous $K_2CO_3$ (540 kg, 3.91 mol) and sodium iodide (18 gm, 120 mmol) in anhydrous acetone (3 L) was added methyl 2-chloropropionate (180 g, 1.469 mmol) and refluxed for 80 hours. The acetone was distilled off and water (3 L) was added. Crude 8 was extracted into chloroform, dried over $Na_2SO_4$, distilled and hexane (750 ml) was added. The solids were then filtered and recrystallised in methanol to give pure 8 (95 g, 40.4%) as a white powder with an m.p between 96.5-98.2° C.

HPLC: 99%; $^1$HNMR (CDCl$_3$) δ 1.60 (d, 3H, CH$_3$), 2.08 (s, 3H, O=C—CH$_3$), 3.76 (s, 3H, ester), 4.66 (q, 1H, CH), 6.72 (d, 2H, Ar), 7.32 (d, 2H, Ar), 8.04 (bs, 1H, NH)

EXAMPLE 9

2-(4-Amino-phenoxy)-propionic acid (9)

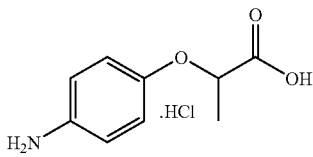

2-(4-Acetylaminophenoxy)-propionic acid methyl ester 8 (320 g, 1.35 mol) in conc. HCl (8 L) was refluxed for 48 hours. Excess conc. HCl was distilled off in vacuum and filtered hot. The mixture was cooled to 10° C., filtered and dried to give pure 9 (240 g, 81.7%) as a brown powder with an m.p between 175-180° C.

EXAMPLE 10

2-(4-Amino-phenoxy)-propionic acid methyl ester (10)

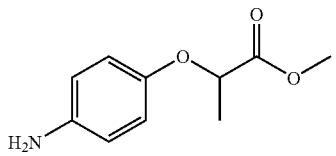

Method-A

Through a mixture of 2-(4-aminophenoxy)-propionic acid 9 (240 g, 1.103 mmol) in methanol (4.8 liters) was passed dry HCl gas at 10° C. for 1 hour followed by reflux for 48 hours. Methanol (2.5 liter) was distilled off, ice water (1 liter) was added and the pH was adjusted to 7.5 with $K_2CO_3$. Crude 10 was extracted into chloroform, washed with 5% $NaHCO_3$ solution, water, dried over $Na_2SO_4$ and distilled to give 10 (80 g, 37.2%) as a brown syrup.

Method-B 2-(4—Nitrophenoxy)-propionic acid methyl ester 14 (20 g, 88.88 mmol) was dissolved in dimethyl formamide (100 ml) in a pressure vessel, Raney nickel (20 grams) was added and the mixture stirred under an atmosphere of hydrogen (4 kg) for 6 hours. The catalyst was removed by filtration and the dimethyl formamide distilled off under vacuum. Crude 10 was purified by column chromatography on silica gel using chloroform as eluant to get pure 10 (15 g, 86.55%) as a brown syrup.

$^1$HNMR ($CDCl_3$) δ 1.56 (d, 3H, $CH_3$), 2.9 (bs, 2H, $NH_2$), 3.72 (s, 3H, ester), 4.58 (q, 1H, CH), 6.53 (d, 2H, Ar), 6.68 (d, 2H, Ar)

EXAMPLE-11

2-(4-Isocyanato-phenoxy)-propionic acid methyl ester (11)

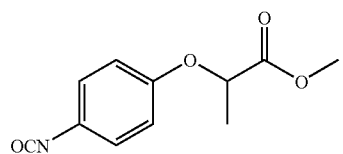

To a mixture of 2-(4-aminophenoxy)-propionic acid methyl ester 10 (15 g, 76.9 mmol) and triethylamine (15.6 g, 154.16 mmol) in toluene (210 ml) under nitrogen atmosphere was added triphosgene (8.4 g, 28.3 mmol) in one lot. Later the reaction mixture was heated to 75° C. over a period of one hour and maintained at this temperature for 26 hours. The reaction mixture was cooled to room temperature, the solids filtered off, and the toluene was distilled off under vacuum to get crude 11, which was vacuum distilled to get pure II (9 grams, 52.9%) as a light yellow syrup.

EXAMPLE 12

2-[4-(2-Hydroxy-ethoxycarbonylamino)-phenoxy]-propionic acid methyl ester (12)

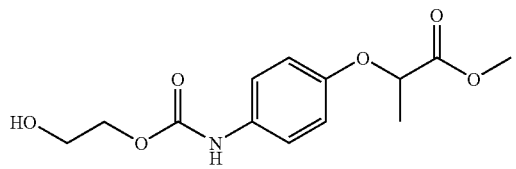

2-(4-Isocyanatophenoxy)-propionic acid methyl ester 11 (20 g, 90.49 mmol) was added to ethylene glycol (40 ml) at room temperature. The reaction was exothermic and the temperature rose to 58° C. This was followed by stirring at room temperature for 16 hours. Water (150 ml) was added and crude 12 was extracted in to chloroform, washed with water (2×50 ml), dried over sodium sulphate and distilled. Crude 12 was purified by column chromatography on silica gel using chloroform as eluant to get pure 12 (13 g, 50.76%) as a syrup which crystallized in 48 hours as a white powder with an m.p between 90.5-92.8° C.

EXAMPLE-13

2-(4-{2-[4-(1-Methoxycarbonyl-ethoxy)-phenylcarbamoyloxy]-ethoxycarbonylamino}-phenoxy)-propionic acid methyl ester (13)

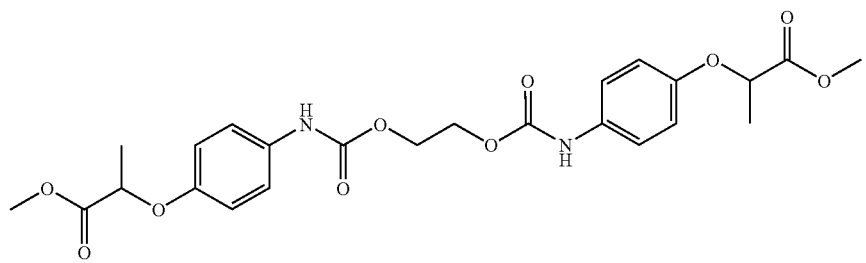

To 2-[4-(2-Hydroxyethoxycarbonylamino)-phenoxy]-propionic acid methyl ester 12 (5 g, 17.66 mmol) in toluene (50 ml) was added 2-(4-Isocyanatophenoxy)-propionic acid methyl ester 13 (3.9 g, 17.64 mmol) at room temperature and heated to 60° C. for 30 hours. Toluene was distilled off and water (50 ml) was added. The solid was filtered and dried to give crude 13, which was purified by column chromatography on silica gel using chloroform as eluant to get pure 13 (5.5 g, 61.8%) as a white powder with an m.p between 98-100° C.

EXAMPLE 14

2-(4-Nitrophenoxy)-propionic acid methyl ester (14)

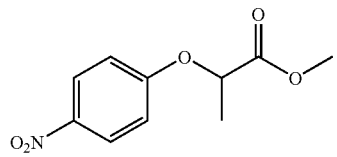

To a mixture of 4-nitrophenol (200 grm, 1.439 mol), anhydrous $K_2CO_3$ (800 grm, 5.789 mol) and sodium iodide (10 g, 66.7 mmol) in anhydrous acetone (2.75 L) was added methyl 2-chloropropionate (264 g, 2.154 mol) and refluxed for 20 hours. Acetone was distilled off and water (3 L) was added. Crude 14 was filtered, dried and recrystallised from a mixture of ethyl acetate:hexane (1:5) to give pure 14 (100 g, 31%) as a white fluffy powder with a m.p between 83-84° C.

EXAMPLE 15

6-(4-Acetylaminophenoxy)-hexanoic acid methyl ester (15)

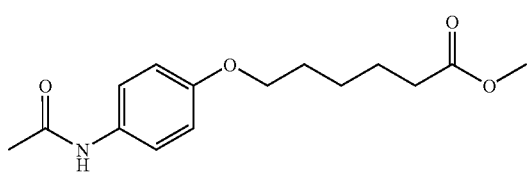

To a mixture of paracetamol (250 gm, 1.654 mmol), anhydrous $K_2CO_3$ (800 gm, 5.789 mmol) and sodium iodide (17 g, 113 mmol) in anhydrous acetone (5 L) was added methyl 6-bromohexanoate (470 g, 2.25 mmol) and refluxed for 60 hours. Acetone was distilled off and water (3 L) was added. Crude 15 was filtered, dried and recrystallised from a mixture of chloroform:hexane (1:5) to give pure 15 (195 g, 66%) as a white powder with an m.p between 96.4-98.8° C.

HPLC: 99%; $^1$HNMR (CDCl$_3$) δ 1.54 (m, 2H, CH$_2$), 1.80 (m, 4H, CH$_2$), 2.14 (s, 3H, O=C—CH$_2$), 2.38 (t, 2H, CH$_2$), 3.68 (s, 3H, ester), 3.92 (t, 2H, OCH$_2$), 6.68 (d, 2H, Ar), 7.05 (bs, 1H, NH), 7.38 (d, 2H, Ar).

EXAMPLE 16

6-(4-Amino-phenoxy)hexanoic acid hydrochloride (16)

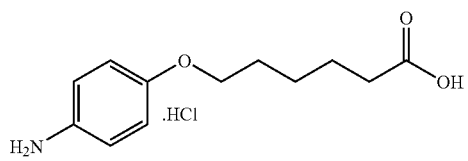

6-(4-acetylaminophenoxy)-hexanoic acid methyl ester 15 (290 g, 1.04 mol), in conc. HCl (7.12 L) was refluxed for 48 hours. Excess conc. HCl was distilled off in vacuum and filtered hot. The mixture was cooled to 10° C., filtered and dried to give pure 16 (150 g, 55.6%) as a brown powder with an m.p between 155-160° C.

EXAMPLE 17

6-(4-Aminophenoxy)-hexanoic acid methyl ester (17)

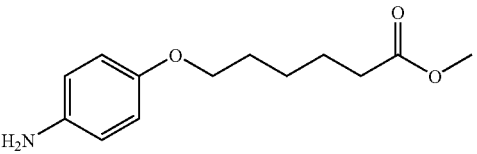

Method-A

Through a mixture of 6-(4-aminophenoxy)-hexanoic acid hydrochloride 16 (150 g, 578 mmol) in methanol (3 L) was passed dry HCl gas at 10° C. for 1 hour and refluxed for 48 hours. Methanol (1.5 L) was distilled off, ice water (1 L) was added and the pH adjusted to 7.5 with $K_2CO_3$. Crude 17 was extracted into chloroform, washed with 5% NaHCO$_3$ solution, then water, and then dried over Na$_2$SO$_4$ and distilled to give 17 (60 g, 43.8%) as a thick brown syrup.

Method-B 6-(4—Nitrophenoxy)-hexanoic acid methyl ester 21 (40 g, 149.81 mmol) was dissolved in dimethyl formamide (200 ml) in a pressure vessel. Raney nickel (20 g) was added and the mixture stirred under an atmosphere of hydrogen (4 kg) for 16 hours. Catalyst was removed by filtration and dimethyl formamide distilled off under vacuum. Crude 17 was purified by column chromatography on silica gel using chloroform as eluant to get pure 17 (28 grams, 78.8%) as a thick brown syrup.

$^1$HNMR (CDCl$_3$) δ 1.5 (m, 2H, CH$_2$), 1.72 (m, 4H, CH$_2$), 2.34 (t, 2H, CH$_2$), 3.66 (s, 3H, ester), 3.85 (t, 2H, OCH$_2$), 6.56 (d, 2H, Ar), 6.68 (d, 2H, Ar).

EXAMPLE-18

6-(4-Isocyanatophenoxy)-hexanoic acid methyl ester (18)

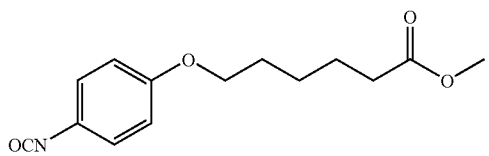

To 6-(4-aminophenoxy)-hexanoic acid methyl ester 17 (26 g, 109.7 mmol) and triethylamine (29.2 g, 288.56 mmol) in toluene (390 ml) under nitrogen atmosphere was added triphosgene (15.6 g, 52.56 mmol) in one lot. The reaction was exothermic and internal temperature rose to 60° C. Later the reaction mixture was heated to 75° C. over a period of one hour and maintained at this temperature for 26 hours. The reaction mixture was cooled to room temperature, the solids filtered off, and toluene distilled off under vacuum to get crude 18, which was vacuum distilled to get pure 18 (10 g, 34.7%) with an m.p between 47-50° C.

EXAMPLE-19

6-[4-(2-Hydroxyethoxycarbonylamino)-phenoxy]-hexanoic acid methyl ester (19)

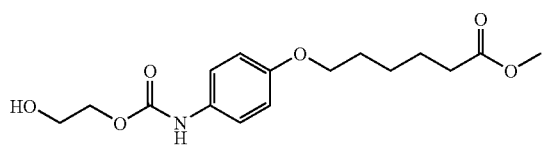

6-(4-Isocyanatophenoxy)-hexanoic acid methyl ester 18 (15 g, 57 mmol) was added to ethylene glycol (50 ml) at room temp. The reaction was exothermic and the temp. rose to 46° C. Stirring at room temp. for 16 h. was followed by addition of water (150 ml), after which crude 19 was filtered, dried and recrystallised from toluene to get pure 19 (12 g, 84%) as a white powder with an m.p. between 69.5-71.5° C.

EXAMPLE-20

6-(4-{2-[4-(5-Methoxycarbonyl-pentyloxy)-phenyl-carbamoyloxy]-ethoxycarbonylamino}-phenoxy)-hexanoic acid methyl ester(20)

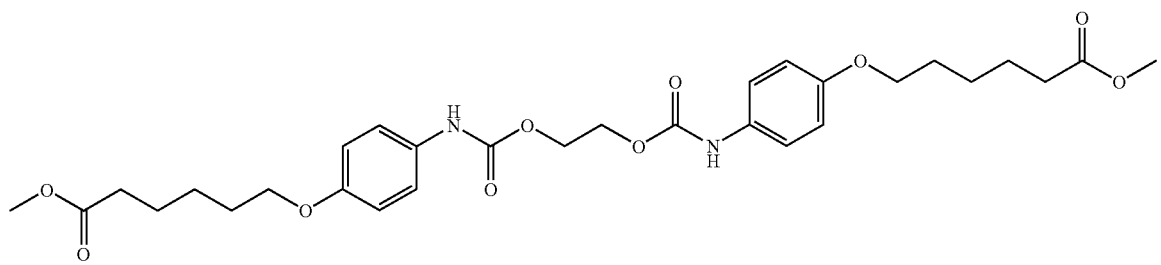

To a mixture of 6-[4-(2-hydroxyethoxycarbonylamino) phenoxy]hexanoic acid methyl ester 19 (5 g, 15.38 mmol) in toluene (50 ml) was added 6-(4-isocyanatophenoxy)-hexanoic acid methyl ester 18 (4 g, 15.2 mmol) at room temperature and heated to 60° C. for 2 hours. Toluene was distilled and water (50 ml) was added. The solid was filtered and dried to give crude 20, which was purified by column chromatography on silica gel using chloroform as eluant to get pure 20 (8.5 g, 94%) as a white powder with an m.p. between 118-120.5° C.

EXAMPLE-21

6-(4-Nitrophenoxy)-hexanoic acid methyl ester (21)

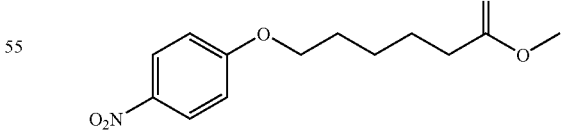

To a mixture of 4-nitrophenol (150 g, 1.079 moles), potassium carbonate (600 g, 4.341 moles) and sodium iodide (10 g, 66.7 mmol) in anhydrous acetone (2.1 L) was added methyl 6-bromohexanoate (156 g, 746.41 mmol) with and heating to reflux for 48 hours. Acetone was distilled off and water (2 L) was added. Crude 21 was filtered, dried and recrystallised from a mixture of ethyl acetate:hexane (1:6) to get pure 21 (130 g, 45.1%) as a white powder with an m.p. between 84.5.5-86.6° C.

EXAMPLE 22

(4-Nitrophenoxy)acetic acid (22)

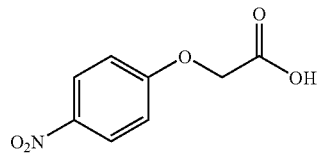

Methyl (4-nitrophenoxy) acetate 7 (100 g, 474 mmol) was refluxed in conc. HCl (1 L) for 8 hours. The reaction mass was cooled to room temperature and crude 22 was filtered, dried and recrystallised from a mixture of ethyl acetate:hexane (1:5) to give pure 22 (86 g, 92.1%) as a white shining powder with an m.p. between 186-188.5° C.

EXAMPLE 23

(4-Nitrophenoxy)-acetic acid-2-hydroxy-ethyl ester (23)

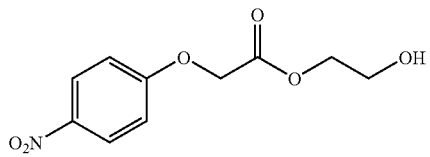

Dry HCl gas was passed through a mixture of (4-nitrophenoxy) acetic acid 22 (100 g, 507 mmol) and ethylene glycol (300 ml) for 1 hour. During HCl gas bubbling the temperature rose to 60° C. The crude reaction mass was poured onto ice (2 kg). Crude 23 was filtered, dried and purified by column chromatography on silica gel using hexane:ethyl acetate (95:5) to give pure 23 (70 g, 57.4%) as a white powder with an m.p. between 73.5-75.5° C.

$^1$HNMR (CDCl$_3$) δ 3.70 (m, 2H, CH$_2$), 4.28 (m, 2H, $$\overset{O}{\underset{\|}{C}}-OCH_2),$$

4.56 (6m, 1H, OH), 4.80 (s, 2H, OCH$_2$), 7.00 (d, 2H, Ar), 8.16 (d, 2H, Ar)

EXAMPLE 24

(4—Nitrophenoxy)-acetic acid-2-[2-(4-nitrophenoxy)-acetoxy]-ethyl ester (24)

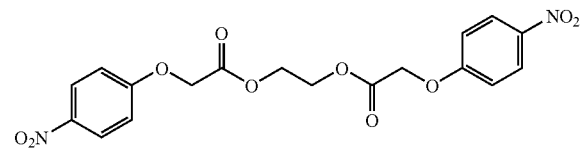

To a mixture of (4-nitrophenoxy) acetic acid 22 (80 g, 406 mmol) and (4-nitrophenoxy)-acetic acid-2-hydroxyethyl ester 23 (80 g, 332 mmol) in anhydrous dichloromethane (2 L) under nitrogen atmosphere was added a solution of 1,3-dicyclohexyl carbodiimide (128 g, 620 mmol) in anhydrous dichloromethane (750 ml) drop wise. The reaction mixture was stirred at room temperature for 8 hours. The solids were filtered off and dichloromethane distilled off to get crude 24. The crude 24 was purified by column chromatography on silica gel using hexane:ethyl acetate (95:5) to get pure 24 (75 grams, 54%) as a white powder with an m.p. between 138-139° C.

EXAMPLE 25

(4-Amino-phenoxy)-acetic acid-2-[2-(4-amino-phenoxy)-acetoxy]-ethyl ester (25)

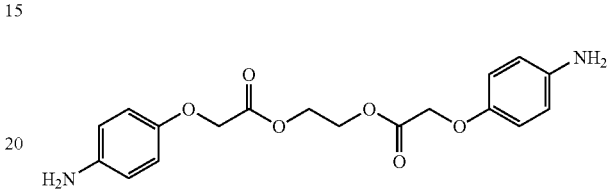

(4—Nitrophenoxy)-acetic acid-2-[2-(4-nitrophenoxy)-acetoxy]-ethyl ester 24 (100 g, 238 mmol) was dissolved in dry dimethyl formamide (500 ml) in a pressure vessel, palladium on carbon (5%, 22 g) was added, and the mixture stirred under an atomsphere of hydrogen (4 kg) for 6 hours. The catalyst was removed by filtration and ice water (2.5 L) was added to the filtrate. Crude 25 was filtered off, dried and recrystallised in a mixture of methanol:chloroform (1:1) to give pure 25 (65 g, 78%) as a light brown shining powder with an m.p. between 124-125.8° C.

$^1$HNMR (CDCl$_3$) δ 4.40 (s, 2H,

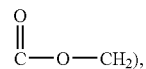

4.50 (s, 2H, OCH$_2$), 6.54 (d, 2H, Ar), 6.70 (d, 2H, Ar), 7.26 (s, 2H, NH$_2$)

EXAMPLE 26

(4-Isocyanatophenoxy)-acetic acid 2-[2-(4-isocyanatophenoxy)-acetoxy]-ethyl ester(26)

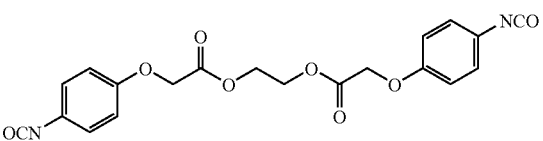

(4-Aminophenoxy)-acetic acid 2-[2-(4-aminophenoxy)-acetoxy]-ethyl ester 25 (5 g, 14.3 mmol) were dissolved in dry dioxane (80 ml) under nitrogen atmosphere and cooled to below 20° C. A solution of triphosgene (7 g, 23.6 mmol) in dry dioxane (20 ml) was added drop wise. The mixture was heated slowly to 75-80° C. and maintained for 2½ hours. The condenser was then arranged for distillation and solvent removed by distillation at atmospheric pressure until the volume of the reaction mixture was reduced to approximately one third. Fresh dry dioxane (50 ml) was added and the solvent was distilled off under vacuum. The residue was re-evaporated two times from dry dioxane to give crude 26. Crude 26 was recrystallised from a mixture of toluene:hexane (1:3) to give pure 26 (2.6 g, 44.2%) as a white powder with an m.p. between 96-98° C.

$^1$HNMR (CDCl$_3$) δ 4.45 (s, 2H,

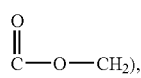

4.62 (s, 2H, OCH$_2$), 6.85 (d, 2H, Ar), 7.04 (s, 2H, Ar); IR: 2274.3 Cm$^{-1}$

EXAMPLE-27

[4-(2-Hydroxy-ethoxycarbonylamino)-phenoxy]-acetic acid 2-{2-[4-(2-hydroxy-ethoxy carbonyl amino)-phenoxy]-acetoxy}-ethyl ester (27)

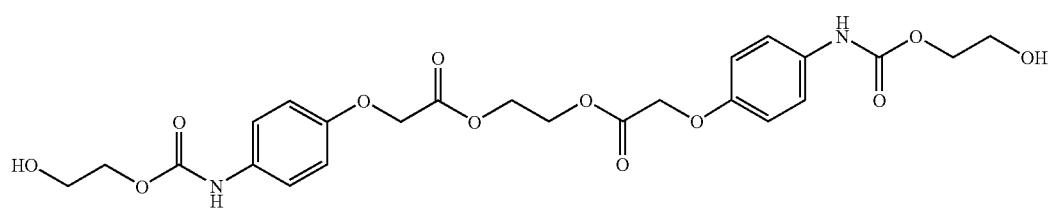

(4-Isocyanatophenoxy)-acetic acid 2-[2-(4-isocyanatophenoxy)-acetoxy]-ethyl ester 26 (0.5 g, 1.21 mmol) was added to ethylene glycol (2.5 ml) at room temperature and further stirred for 17 hours. Water (10 ml) was added, and the solid then filtered, dried and recrystallised from methanol to get pure 27 (0.4 g, 61.5%) as a white powder with an m.p. between 158-161° C.

EXAMPLE-28

(4-Amino-phenoxy)-acetic acid 2-hydroxy-ethyl ester (28)

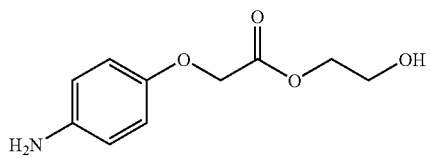

(4—Nitrophenoxy)-acetic acid-2-hydroxyethyl ester 23 (1 g, 4.15 mmol) was dissolved in ethyl acetate in a pressure vessel. Palladium on carbon (5%, 0.5 g) was added and the mixture stirred under an atmosphere of hydrogen (0.5 kg) for one hour. Catalyst was removed by filtration, the ethyl acetate distilled off and hexane added. The solid product was filtered and dried to give pure 28 (0.2 g 22.8%) as a brown powder with an m.p. between 104-106.3° C.

EXAMPLE 29

2-(4-Nitrophenoxy)-propionic acid (29)

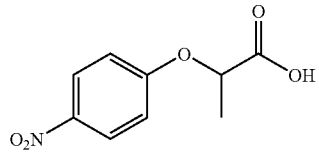

2-(4-Nitrophenoxy)propionic acid methyl ester 14 (50 g) and concen. HCl (500 ml) were refluxed for 8 hours. The reaction mass was cooled to room temperature. Crude 29 was filtered, dried and recrystallised from a mixture of ethyl acetate:hexane (1:5) to give pure 29 (40 g, 85.3%) as a white powder with an m.p. between 139-141° C.

EXAMPLE 30

2-(4-Nitrophenoxy)-propionic acid 2-hydroxy-ethyl ester (30)

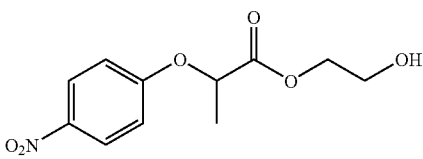

Dry HCl gas was passed through a mixture of 2-(4-nitrophenoxy)-propionic acid 29 (45 g, 213 mol) and ethylene glycol (135 ml) for 1½ hours. During HCl gas bubbling the temperature rose to 60° C. The crude reaction mass was poured onto cold water (600 ml). Crude 30 was extracted into chloroform, dried over Na$_2$SO$_4$, distilled and purified by column chromatography on silica gel using hexane as eluant to give pure 30 (28 g, 56.8%) as a syrup.

$^1$HNMR (CDCl$_3$) δ 1.62 (d, 3H, CH$_3$), 2.64 (bs, 1H, OH), 3.68 (m, 2H, CH$_2$), 4.20 (m, 2H, CH$_2$), 4.82 (q, 1H, OCH), 6.85 (d, 2H, Ar), 8.05 (d, 2H, Ar)

EXAMPLE 31

2-(4-Nitrophenoxy)propionic acid 2-[2-(4-nitrophenoxy)propionyloxy]ethyl ester (31)

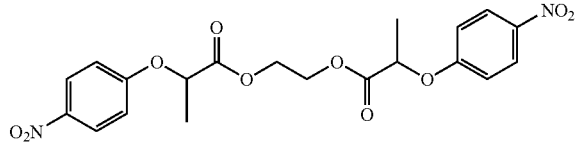

To a mixture of 2-(4-nitrophenoxy)-propionic acid 29 (25 g, 118.5 mmol) and 2-(4-nitrophenoxy)propionic acid 2-hydroxyethyl ester 30 (25 g, 108 mmol) in anhydrous dichloromethane (625 ml) under nitrogen atmosphere was added dropwise a solution of 1,3-dicyclohexyl carbodiimide (40 g, 194 mmol) in anhydrous dichloromethane (250 ml). The reaction mixture was stirred at room temperature for 8 hours. The solids were filtered off and dichloromethane distilled off to get crude 31. The crude 31 was purified by column chromatography on silica gel using hexane as eluant to get pure 31 (17 g, 35.1%) as a white powder with an m.p. between 117.5-120.5° C.

$^1$HNMR (DMSO) δ 1.50(d, 3H, CH$_3$), 4.36 (s, 2H,

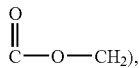

5.22 (q, 1H, OCH), 7.08 (d, 2H, Ar), 6.16 (d, 2H, Ar)

EXAMPLE 32

2-(4-Aminophenoxy)-propionic acid 2-[2-(4-aminophenoxy)-propionyloxy]-ethyl ester (32)

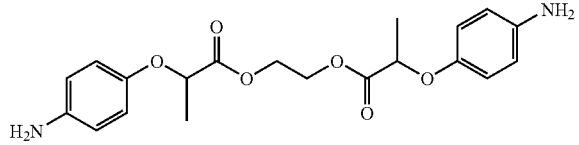

2-(4—Nitrophenoxy)-propionic acid 2-[2-(4-nitrophenoxy)propionyloxy]-ethyl ester 31 (50 g, 89.3 mmol) was dissolved in dry dimethylformamide (400 ml) in a pressure vessel. Palladium on carbon(5%, 12.5 g) was added, and the mixture stirred under an atmosphere of hydrogen (4 kg) for 4 hours. Catalyst was removed by filtration and ice water (3 L) was added to the filtrate. Crude 32 was extracted into ethyl acetate, dried over Na$_2$SO$_4$, and distilled and purified by column chromatography on silica gel using chloroform as eluant to give pure 32 (25 g, 58%) as a syrup.

$^1$HNMR (CDCl$_3$) δ 1.52 (d, 3H, CH$_3$), 3.30 (bs, 2H, NH$_2$), 4.30(s, 2H,

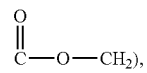

EXAMPLE 33

2-(4-Isocyanatophenoxy)-propionic acid 2-[2-(4-isocyanatophenoxy)-propionyloxy]-ethyl ester (33)

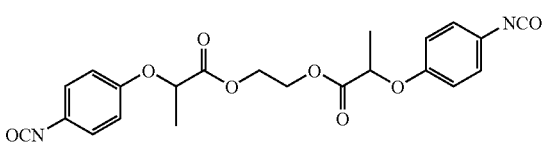

2-(4-Aminophenoxy)-propionic acid 2-[2-(4-aminophenoxy)-propionyloxy]-ethyl ester 32 (5.3 g, 13.6 mmol) was dissolved in dry dioxane (80 ml) under nitrogen atmosphere and cooled to below 20° C. A solution of triphosgene (7 g, 23.6 mmol) in dry dioxane (20 ml) was added drop wise. The mixture was heated slowly to 75-80° C. and maintained for 2½ hours. The condenser was then arranged for distillation and solvent removed by distillation at atmospheric pressure until the reaction mixture volume was reduced to approximately one third. Fresh dry dioxane (50 ml) was added and the solvent then distilled off under vacuum. The residue was re-evaporated two times from dry dioxane to give pure 33 (4 g, 66.5%) as a light brown liquid.

$^1$HNMR (CDCl$_3$) δ 1.60 (d, 3H, CH$_3$), 4.41 (s, 2H, COOCH$_2$) 4.68 (q, 1H, OCH), 6.84 (d, 2H, Ar), 7.00 (d, 2H, Ar)

EXAMPLE 34

2-[4-(2-Hydroxyethoxycarbonylamino)-phenoxy]-propionic acid 2-{2-[4-(2-hydroxy-ethoxycarbonylamino)-phenoxy]-propionyloxy}-ethyl ester (34)

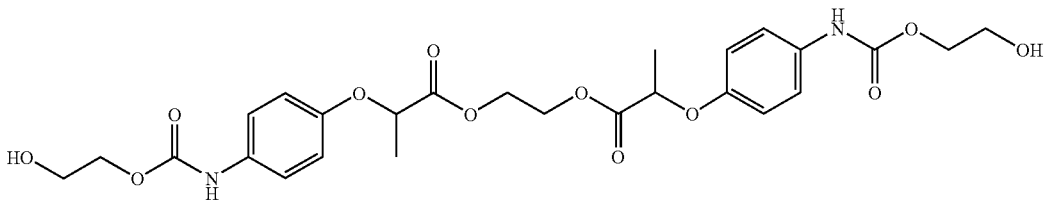

2-(4-Isocyanatophenoxy)-propionic acid 2-[2-(4-isocyanatophenoxy)-propionyloxy]-ethyl ester 33 (0.5 g, 1.1 mmol) was added to ethylene glycol (2.5 ml) at room temp. and stirred for 6 hours. Water (10 ml) was added, followed by extraction into ethyl acetate, drying over sodium sulphate and distilling to get crude 34, which was purified by column chromatography on silica gel using hexane:ethyl acetate (1:1) to get pure 34 (0.1 g, 15.6%).

EXAMPLE-35

6-(4—Nitrophenoxy)-hexanoic acid (35)

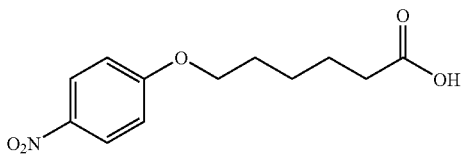

6-(4-nitrophenoxy)-hexanoic acid methyl ester 21 (125 g, 468.16 mmol) was refluxed in conc. HCl (1250 ml) for 16 hours. The reaction mixture was cooled to room temp., filtered, dried and recrystallised from a mixture of ethyl acetate:hexane (1:6) to get pure 35 (95 g, 80.2%) as a white powder with an m.p. between 104-107° C.

EXAMPLE-36

6-(4-Nitrophenoxy)-hexanoic acid 2-hydroxy-ethyl ester (36)

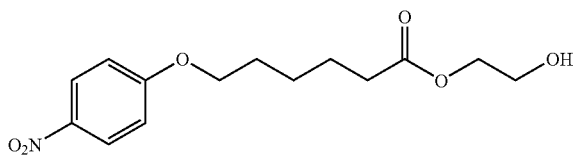

Dry HCl gas was passed through a mixture of 6-(4-nitrophenoxy)-hexanoic acid 35 (50 g, 197.62 mmol) and ethylene glycol (200 ml) was passed dry HCl gas for one hour. During HCl gas bubbling the temperature rose to 60° C. The crude reaction mass was poured onto ice (1 kg), extracted in to ethyl acetate, washed with water (2×250 ml), dried over sodium sulphate and distilled to get crude 36, which was purified by column chromatography on silica gel using benzene as eluant to get pure 36 (46 g, 78.3) as a light yellow syrup.

EXAMPLE 38

2-(4-Nitrophenoxy)-propionic acid 2-[2-(4-nitrophenoxy)-acetoxy]-ethyl ester (38)

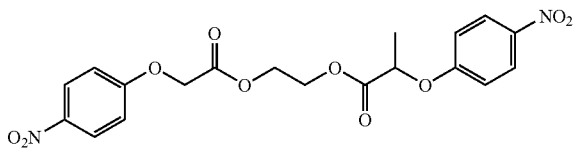

To a mixture of [4-nitrophenoxy]-acetic acid-2-hydroxy-ethyl ester 23 (100 grams, 410 mmol) and 2-(4-nitrophenoxy)-propionic acid 29 (95 g, 450 mmol ) in anhydrous dichloromethane (1000 ml) under nitrogen atmosphere was added dropwise a solution of 1,3-dicyclohexyl carbodiimide (240 g, 1160 mmol) in anhydrous dichloromethane (600 ml). The reaction mixture was stirred at room temperature for 12 hrs. The solids were filtered off and dichloromethane distilled off to get crude 38. The crude 38 was purified by column chromatography on silica gel using benzene as eluant to give pure 38 (53 grams, 29%) as a yellow low melting solid.

$^1$HNMR (CDCl$_3$) δ 1.66 (d, 3H, CH$_3$), 4.40 (m, 4H, OCH$_2$), 4.58 (s, 2H, OCH$_2$), 4.81 (q, 1H, OCH), 6.92 (m, 4H, Ar), 8.16 (m, 4H, Ar)

EXAMPLE 39

2-(4-Aminophenoxy)-propionic acid 2-[2-(4-aminophenoxy)-acetoxy]-ethyl ester (39)

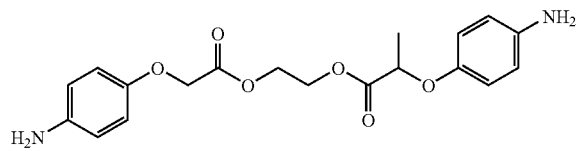

2-(4-Nitrophenoxy)propionic acid 2-[2-(4-nitrophenoxy)acetoxy]-ethyl ester 38 (20 g, 50 mmol) was dissolved in dry dimethylformamide (150 ml) in a pressure vessel. Palladium on carbon (5%, 5 g) was added and the mixture stirred under an atmosphere of hydrogen (4 kg) for 3 hrs. The catalyst was removed by filtration and ice water (1L) added to the filtrate. Crude 39 was extracted into ethyl acetate, dried over Na$_2$SO$_4$, distilled and purified by column chromatography on silica gel using chloroform:ethyl acetate (8:2) to give pure 39 (10 g, 58%) as a dark brown syrup.

$^1$HNMR (CDCl$_3$) δ 1.5 (d, 3H, CH$_3$) 4.30 (s, 4H, OCH$_2$), 4.46 (s, 2H, OCH$_2$), 4.56 (q, 1H, OCH), 6.50 (m, 4H, Ar), 6.62 (m, 4H, Ar); IR: 3363.9 Cm$^{-1}$

EXAMPLE 40

2-(4-Isocyanatophenoxy)-propionic acid 2-[2-(4-isocyanatophenoxy)-acetoxy]-ethyl ester (40)

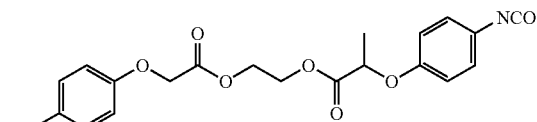

2-(4-Aminophenoxy)-propionic acid 2-[2-(4-aminophenoxy)-acetoxy]-ethyl ester 39 (5.2 g, 13.9 mmol) was dissolved in dry dioxane (80 ml) under nitrogen atmosphere and cooled to below 20° C. A solution of triphosgene (7 g, 23.6 mmol) in dry dioxane (20 ml) was added drop wise. The mixture was heated slowly to 75-80° C. and maintained for 3 hrs. A condenser was then arranged for distillation and solvent removed by distillation at atmospheric pressure until the volume of the reaction mixture was reduced to approximately one third. Fresh dry dioxane (50 ml) was added and the solvent was distilled off under vacuum. The residue was re-evaporated two times from dry dioxane to give 40 (2.2 g, 37.2%) as a light yellow syrup.

IR: 2270 Cm$^{-1}$; $^1$HNMR (CDCl$_3$) δ 1.62 (d, 3H, CH$_3$) 4.40 (m, 4H, OCH$_2$), 4.52 (s, 2H, OCH$_2$), 4.72 (q, 1H, OCH), 6.80 (m, 4H, Ar), 7.00 (m, 4H, Ar)

EXAMPLE 41

2-[4-(2-Hydroxyethoxycarbonylamino)-phenoxy]-propionic acid 2-{2-[4-(2-hydroxy-ethoxy carbonylamino)-phenoxy]-acetoxy}-ethyl ester (41)

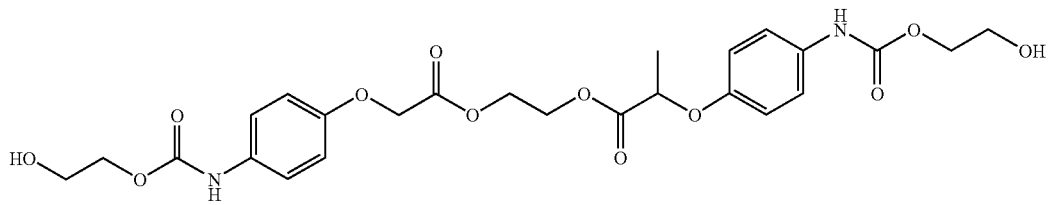

2-(4-Isocyanatophenoxy)-propionic acid 2-[2-(4-isocyanatophenoxy)-acetoxy]-ethyl ester 40 (0.5 g, 1.17 mmol) was added to a solution of ethylene glycol (2.5 ml) in tetrahydrofuran (5 ml) at room temperature and stirred for 3 hours. The tetrahydrofuran was distilled off under vacuum and water (10 ml) was added. Crude 41 was extracted into ethyl acetate, washed with water (2×5ml), dried over sodium sulphate and distilled. Crude 41 was purified by column chromatography on silica gel using chloroform at eluant to get pure 41 (0.1 g, 15.6%) as a light yellow syrup.

EXAMPLE 42

[2-(4-Nitrophenoxy)-ethoxy]acetic acid methyl ester (42)

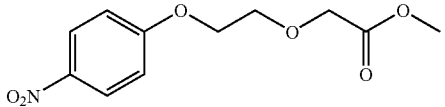

To a mixture of 4-nitrophenol (5 g, 36 mmol), anhydrous $K_2CO_3$ (20 g, 145 mmol) and sodium iodide (2 g, 13.3 mmol) in anhydrous acetone (100 ml) was added (2-bromoethoxy) acetic acid methyl ester (11 g, 56 mmol) and then refluxed for 24 hours. Acetone was distilled off and water (100 ml) was added. Crude 42 was filtered, dried and purified by column chromatography on silica gel using benzene as eluant to give pure 42 (4 g, 43.6%) as a white fluffy powder with an m.p. between 96-97.8° C.

$^1$HNMR (CDCl$_3$+DMSO) δ 3.72 (s, 3H, ester), 3.94 (t, 2H, OCH$_2$), 4.18 (s, 2H, OCH$_2$), 4.30 (t, 2H, OCH$_2$), 7.08 (d, 2H, Ar), 8.18 (d, 2H, Ar)

EXAMPLE 43

[2-(4-Aminophenoxy)-ethoxy]-acetic acid methyl ester (43)

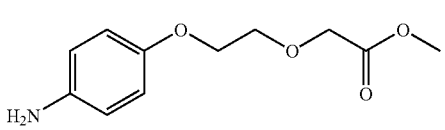

[2-(4-Nitrophenoxy)ethoxy]acetic acid methyl ester 42 (1 g, 3.9 mmol) was dissolved in anhydrous ethyl acetate (20 ml). Palladium on carbon (10%, 0.1 g) was added and the mixture stirred under a hydrogen atmosphere using a balloon for 30 mins. The catalyst was filtered, the filtrate concentrated, hexane (3 ml) added, and the solid filtered to give 43(625 mg, 70.9%) as a light brown powder with a m.p. between 51-52.5° C.

$^1$HNMR (CDCl$_3$) δ 3.04 (bs, 2H, NH$_2$), 3.72 (s, 3H, ester), 3.88 (t, 2H, OCH$_2$), 4.08 (t, 2H, OCH$_2$), 4.20 (s, 2H, OCH$_2$), 6.58 (d, 2H, Ar), 6.70 (d, 2H, Ar)

EXAMPLE 44

(4-Nitrophenoxy)-acetic acid methoxycarbonylmethyl ester (44)

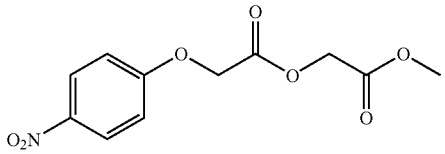

To a mixture of (4-nitrophenoxy) acetic acid 22 (150 g, 761.4 mmol) and triethylamine (85 g, 840 mmol) in acetone (750 ml) was added methyl chloroacetate (91.6 g, 844 mmol) drop wise and stirred under reflux for 8 hours. Solids were filtered off and poured onto cold 5% sodium bicarbonate solution (4 L). Crude 44 was filtered, dried and recrystallised from chloroform:hexane (1:6) to get pure 44 (186 g, 90.8%) as a white powder with an m.p. between 88-90° C.

$^1$H NMR (CDCl$_3$) δ 3.80 (s, 3H, Ester), 4.75 (s, 2H, OCH$_2$), 4.88 (s, 2H, OCH$_2$), 7.02 (d, 2H, Ar), 8.22 (d, 2H, Ar)

EXAMPLE 45

(4-Aminophenoxy)-acetic acid methoxycarbonylmethyl ester (45)

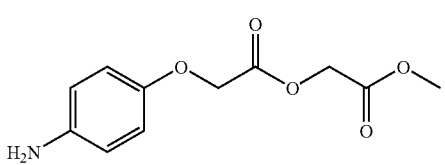

(4-Nitrophenoxy)-acetic acid methoxycarbonyl methyl ester 44 (20 g, 74.3 mmol) was dissolved in dimethyl formamide (100 ml) in a pressure vessel. Palladium on carbon (5%, 8 g) was added, and the mixture stirred under an atmosphere of hydrogen (4 kg) for 2 hours. The catalyst was removed by filtration and ice water (400 ml) was added to the filtrate. Crude 45 was extracted into ethyl acetate, dried over $Na_2SO_4$ and distilled. Crude 45 was then recrystallised from chloroform:hexane (1:6) to get pure 45 (13 g, 73%) as a light brown shining powder with an m.p. between 76.5-78.5° C.

$^1$H NMR ($CDCl_3$) δ 3.32 (bs, 2H, $NH_2$), 3.76 (s, 3H, Ester), 4.70 (s, 2H, $OCH_2$), 4.74 (s, 2H, $OCH_2$), 6.60 (d, 2H, Ar), 6.74 (d, 2H, Ar)

EXAMPLE 46

(4-Cyanatophenoxy)-acetic acid methoxycarbonyl methyl ester (46)

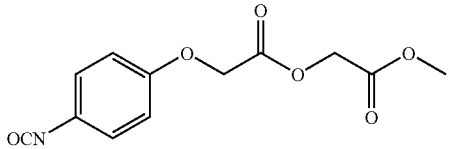

(4-Aminophenoxy)-acetic acid methoxycarbonyl methyl ester 45 (10 g, 41.84 mmol) was dissolved in dry dioxane (200 ml) under nitrogen atmosphere and cooled below 20° C. A solution of triphosgene (10.5 g, 35.38 mmol) in dry dioxane (50 ml) was added drop wise. The mixture was heated slowly to 70-75° C. and maintained for 2½ hours. The condenser was then arranged for distillation and the solvent removed by distillation at atmospheric pressure until the volume of the reaction mixture was reduced to approximately one third. Fresh dry dioxane (125 ml) was added and the solvent distilled off under vacuum. The residue was re-evaporated two times from dry dioxane to give pure 46 (10 g, 90.2%) as a liquid.

IR: 2275.6 $cm^{-1}$; $^1$H NMR ($CDCl_3$) δ 3.80 (s, 3H, Ester), 4.74 (s, 4H, $CH_2×2$), 6.88 (d, 2H, Ar), 7.06 (d, 2H, Ar)

EXAMPLE 47

[4-(2-Hydroxyethoxycarbonylamino)-phenoxy]-acetic acid methoxycarbonyl methyl ester (47)

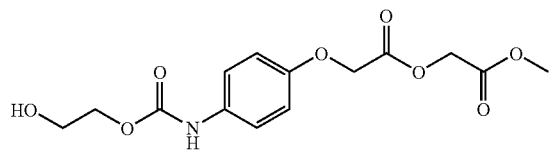

To a solution of (4-cyanatophenoxy)acetic acid methoxycarbonyl methyl ester 46 (5 g 18.85 mmol) in dry tetrahydrofuran (20 ml) was added ethylene glycol (30 ml) with stirring at room temperature for 30 minutes. The reaction mixture was poured onto ice water (100 ml) and crude 47 was extracted into ethyl acetate, dried over sodium sulphate and distilled. Crude 47 was purified by column chromatography on silica gel using chloroform as eluant to get pure 47 (2 g, 32.4%) with an m.p. between 79-82° C.

$^1$H NMR ($CDCl_3$) δ 3.76 (s, 3H, Ester), 3.80 (t, 2H, $CH_2$), 4.25 (m, 2H, $CH_2$), 4.70 (s, 2H, $CH_2$), 4.72 (s, 2H, $CH_2$), 6.84 (d, 2H, Ar), 7.02 (s, 1H, NH), 7.26 (d, 2H, Ar)

EXAMPLE 48

(4-Acetylaminophenoxy)acetic acid methoxycarbonyl methyl ester (48)

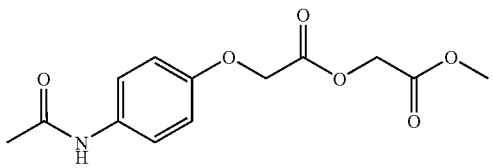

Acetyl chloride was added dropwise to a mixture of 4-aminophenoxyacetic acid methoxycarbonyl methyl ester 45 (3 g, 12.5 mmol) and triethylamine (3.8 g, 37.5 mmol) in acetone (30 ml) at 0° C. and stirred at room temperature for 12 hrs. The solids were filtered, the acetone distilled off and cold water (15 ml) was added. Crude 48 was extracted into chloroform, washed with 5% sodium bicarbonate solution (2×5 ml), water (2×5 ml), dried over sodium sulphate and distilled. Crude 48 was recrystallised from a mixture of chloroform:hexane (1:6) to give pure 48 (3 g, 85%) as an off-white powder. M.p: 98.6-101.5° C.

$^1$H NMR ($CDCl_3$) δ 2.20 (s, 3H, $COCH_3$), 3.78 (s, 3H, ester), 4.70 (s, 4H, $CH_2×2$), 6.82 (d, 2H, Ar), 7.18 (s, 1H, NH), 7.35 (d, 2H, Ar)

EXAMPLE 49

[4-(2-Benzyloxyacetylamino)-phenoxy]-acetic acid methyl ester (49)

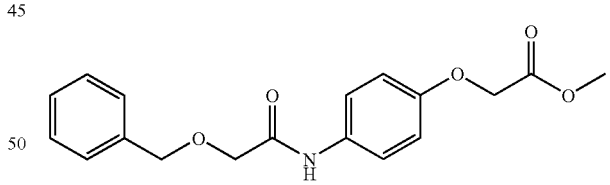

To a mixture of (4-aminophenoxy)-acetic acid methyl ester 3 (20 g, 110.5 mmol) and benzyloxy acetic acid (20.4 g, 123 mmol) in anhydrous dichloromethane (200 ml) under nitrogen atmosphere was added dropwise a solution of 1,3-dicyclohexyl carbodiimide (63.2 g, 306 mmol) in anhydrous dichloromethane (80 ml) then stirred at room temp. for 12 hours. The solids were filtered off, the dichloromethane was washed with 5% sodium bicarbonate solution (100 ml), water (100 ml) added, and the solids dried over sodium sulphate and distilled to get crude 49. Crude 49 was purified by column chromatography on silica gel using benzene as eluant to get pure 49 (25 g, 68.9%) as a white powder with an m.p. between 76-77.5° C.

¹H NMR (CDCl₃) δ 3.82 (s, 3H, ester), 4.10 (s, 2H, CH₂), 4.62 (s, 2H, CH₂), 4.66 (s, 2H, CH₂), 6.88 (d, 2H, Ar), 7.38 (m, 5H, Ar), 7.46 (d, 2H, Ar), 8.24 (bs, 1H, NH)

EXAMPLE 50

[4-(2-Hydroxyacetylamino)-phenoxy]-acetic acid methyl ester (50)

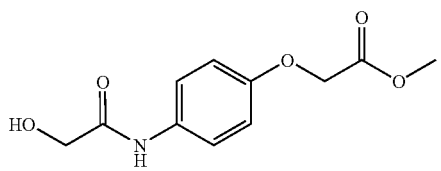

[4-(2-Benzyloxyacetylamino)phenoxy]acetic acid methyl ester 49 (25 g, 76 mmol) was dissolved in methanol (450 ml) in a pressure vessel. Palladium on carbon (5%, 10 g) was added and the mixture stirred under a hydrogen atmosphere (2 kg) for 5 hrs. Catalyst was removed by filtration and methanol distilled off. Crude 50 was recrystallised in chloroform:hexane (1:6) to give pure 50 (14 g) as a white powder with an m.p. between 147.5-150° C.

¹H NMR (CDCl₃+DMSO-d₆): δ 3.74 (s, 3H, ester), 3.96 (d, 2H, CH₂OH), 4.64 (s, 2H, OCH₂), 5.48 (t, 1H, OH), 6.80 (d, 2H, Ar), 7.54 (d, 2H, Ar) 9.2 (bs, 1H, NH)

EXAMPLE 51

2-[4-(2-Benzyloxyacetylamino)-phenoxy]-propionic acid methyl ester (51)

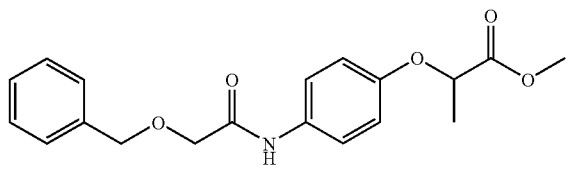

To a mixture of 2-(4-aminophenoxy)-propionic acid methyl ester 10 (20 grams, 102.5 mmol) and triethylamine (23 ml, 165 mmol) in acetone (120 ml) at 0° C. was added dropwise benzyloxy acetyl chloride (28 g, 152 mmol) followed by stirring at room temp for 12 hours. The solids were filtered off, acetone distilled off, and water (100 ml) added. Crude 51 was extracted into chloroform, washed with 5% sodium bicarbonate (2×100 ml) and water (200 ml), then dried over sodium sulphate and distilled. Crude 51 was purified by column chromatography on silica gel using benzene as eluant to get pure 51 (21 g, 59.8%) as a light brown powder with an m.p. between 67-70° C.

¹H NMR (CDCl₃) δ 1.60 (d, 3H, CH₃), 3.72 (s, 3H, Ester), 4.02 (s, 2H, CH₂), 4.62 (s, 2H, CH₂), 4.68 (q, 1H, CH), 6.76 (d, 2H, Ar), 7.30 (m, 5H, Ar), 7.42 (d, 2H, Ar), 8.18 (s, 1H, NH)

EXAMPLE 52

2-[4-(2-Hydroxyacetylamino)-phenoxy]-propionic acid methyl ester (52)

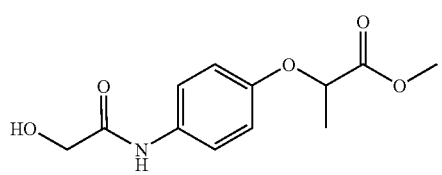

2-[4-(2-Benzyloxyacetylamino)-phenoxy]-propionic acid methyl ester 51 (15 gm, 43.7 mmol) was dissolved in methanol (150 ml) in a pressure vessel. Palladium on carbon (5%, 8 g) was added and the mixture stirred under a hydrogen atmosphere (2.5 kg) for 10 hrs. Catalyst was removed by filtration and the methanol distilled off. The crude 52 was recrystallised in chloroform:hexane (1:6) to give pure 52 (4 g, 36.3%) as a white powder with an m.p. between 111-112.6° C.

¹H NMR (CDCl₃) δ 1.60 (d, 3H, CH₃), 3.44 (bt, 1H, OH), 3.78 (s, 3H, Ester), 4.14 (d, 1H, CH₂OH), 4.72 (q, 1H, CH), 6.80 (d, 2H, Ar), 7.44 (d, 2H, Ar), 8.30 (s, 1H, NH

EXAMPLE 53

6-[4-(2-Benzyloxy-acetylamino)-phenoxy]-hexanoic acid methyl ester (53)

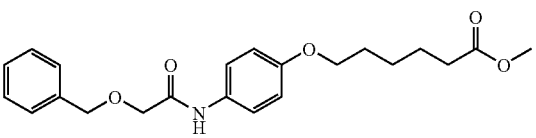

To a mixture of 6-(4-aminophenoxy)-hexanoic acid methyl ester 17 (25 g, 105 mmol) and triethylamine (21.4 g, 211.6 mmol) in acetone (200 ml) at 0° C. was added dropwise benzyloxy acetyl chloride (25 g, 135.5 mmol) followed by stirring at room temp. for 12 hrs. The solids were filtered off, acetone distilled off and water (100 ml) added. Crude 53 was extracted into chloroform, washed with 5% sodium bicarbonate solution (2×100 ml), then water (100 ml), dried over sodium sulphate and distilled. Crude 53 was purified by column chromatography on silica gel using benzene as eluant to get pure 53 (9 g, 22.2%), an off-white powder with a m.p. between 46-49° C.

¹H NMR (CDCl₃) δ 1.52 (m, 2H, CH₂), 1.72 (m, 4H, CH₂×2), 2.32 (t, 2H, CH₂), 3.68 (s, 3H, Ester), 3.92 (t, 2H, CH₂), 4.10 (s, 2H, CH₂), 4.68 (s, 2H, CH₂), 6.82 (d, 2H, Ar), 8.20 (s, 1H, NH)

EXAMPLE 54

6-[4-(2-Hydroxyacetylamino)-phenoxy]-hexanoic acid methyl ester (54)

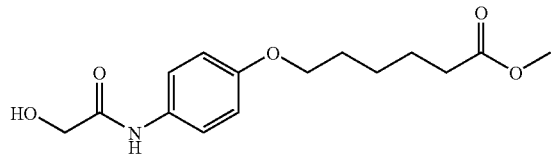

6-[4-(2-Benzyloxyacetylamino)-phenoxy]-hexanoic acid methyl ester 53 (1 grams, 2.6 mmol) was dissolved in methanol (10 ml) in a pressure vessel. Palladium on carbon (5%, 250 mg) was added and the mixture stirred under a hydrogen atmosphere (2 kg) for 5 hrs. Catalyst was removed by filtration and methanol distilled off. Crude 54 was recrystallised in chloroform:hexane (1:6) to get pure 54 (0.5 g, 65.3%) as a white powder with an m.p. between 91.5-94° C.

¹H NMR (CDCl₃) δ 1.45 (m, 2H, CH₂), 1.62 (m, 4H, CH₂×2), 2.36 (t, 2H, CH₂), 3.02 (t, 2H, CH₂), 3.02 (t, 1H, OH), 3.68 (s, 3H, Ester), 3.92 (t, 2H, CH₂), 4.22 (d, 2H, CH₂), 6.84 (d, 2H, Ar), 7.46 (d, 2H, Ar), 8.24 (bs, 1H, NH).

EXAMPLE 55

[4-(2-Hydroxyacetylamino)-phenoxy]-acetic acid methoxycarbonyl methyl ester (55)

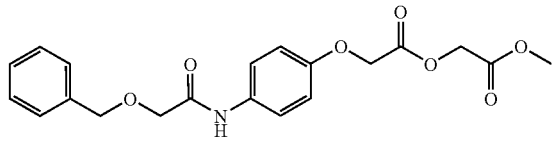

To a mixture of (4-aminophenoxy)-acetic acid methoxycarbonyl methyl ester 45 (5 g, 20.9 mmol) and triethylamine (8.8 ml, 63.1 mmol) in acetone (50 ml) at 0° C. was added dropwise benzyloxy acetyl chloride (5.8 g, 31.4 mmol), followed by stirring at room temp. for 20 hrs. The solids were filtered off, the acetone distilled off and water (50 ml) added. Crude 55 was extracted into chloroform, washed with 5% sodium bi-carbonate (2×50 ml) and water (2×50 ml), dried over sodium sulphate and distilled. Crude 55 was purified by column chromatography on silica gel using chloroform as eluant to get pure 55 (5 g, 61.7%) as a light brown powder with an m.p, between 66.5-69.5° C.

¹H NMR (CDCl₃) δ 3.78 (s, 3H, Ester), 4.06 (s, 2H, CH₂), 4.64 (s, 2H, CH₂), 4.70 (s, 4H, CH₂×2), 6.86 (d, 2H, Ar), 7.34 (m, 5H, Ar), 7.48 (d, 2H, Ar), 8.18 (bs, 1H, NH),

EXAMPLE 56

[4-(2-Hydroxyacetylamino)-phenoxy]-acetic acid methoxycarbonyl methyl ester (56)

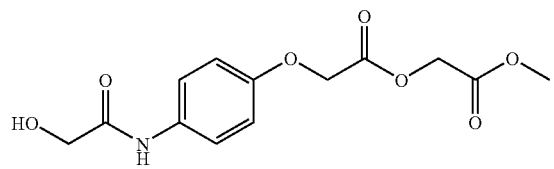

[4-(2-Hydroxyacetylamino)-phenoxy]-acetic acid methoxycarbonyl methyl ester 55 (2 g) was dissolved in methanol (20 ml) in a pressure vessel. Palladium on carbon (5%, 1 g) was added and the mixture stirred under a hydrogen atmosphere (2.5 kg) for 10 hrs. The catalyst was removed by filtration and the methanol distilled off. Crude 56 was purified by column chromatography on silica gel using chloroform as eluant to give pure 56 (0.5 g, 32.5%) as a white powder with an m.p. between 92-95° C.

¹H NMR (CDCl₃+DMSO,d₆) δ 3.75 (s, 3H, Ester), 3.88 (d, 2H, CH₂OH), 4.74 (s, 2H, CH₂), 4.78 (s, 2H, CH₂),5.50(t,1H, OH), 6.84(d,2H,Ar), 7.58(d,2H,Ar), 9.02(s, 1H,NH)

EXAMPLE 57

[4-(6-Benzyloxyhexanoylamino)-phenoxy]-acetic acid methyl ester (57)

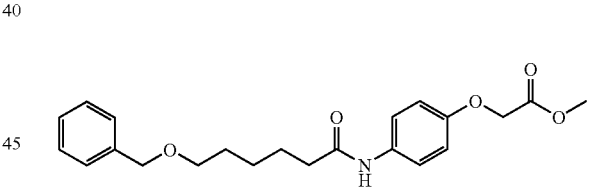

To a mixture of (4-aminophenoxy)-acetic acid methyl ester 3 (20 g, 110.5 mmol) and benzyloxy hexanoic acid (50 g, 225.22 mmol) in anhydrous dichloromethane (300 ml) at 0° C. under nitrogen atmosphere was added dropwise a solution of 1,3-dicyclohexyl carbodiimide (80 g, 387.73 mmol) in anhydrous dichloromethane (100 ml). The reaction mixture was stirred at room temperature for 16 hours. The solids were filtered off, the dichloromethane was washed with 5% sodium bicarbonate solution (2×100 ml), then water (2×100 ml), dried over sodium sulphate and distilled to get crude 57. Crude 57 was purified by column chromatography on silica gel using chloroform as eluant to give 24 grams of [4-(6-Benzyloxyhexanoylamino)-phenoxy]-acetic acid methyl ester which was further purified by recrystallising in chloroform:hexane (1:6) to give pure 57 (20 g, 47%) as a white powder with an m.p. between 64.6-67° C.

¹H NMR (CDCl₃) δ 1.48 (m, 2H, CH₂), 1.68 (m, 4H, CH₂), 2.30 (t, 2H, CH₂), 3.44 (t, 2H, CH₂), 3.78 (s, 3H, ester), 4.44

(s, 2H, CH$_2$), 4.56 (s, 2H, CH$_2$), 6.74 (d, 2H, Ar), 7.30 (m, 5H, Ar), 7.35 (d, 2H, Ar), 7.50 (s, 1H, NH).

EXAMPLE 58

[4-(6-Hydroxyhexanoylamino)-phenoxy]-acetic acid methyl ester (58)

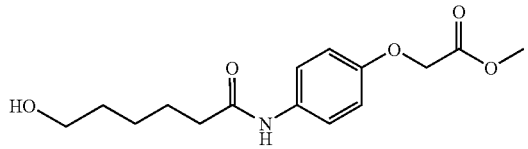

[4-(6-Benzyloxyhexanoylamino)-phenoxy]-acetic acid methyl ester 57 (24 grms, 62.33 mmol) was dissolved in a mixture of methanol (200 ml) and dimethyl formamide (50 ml) in a pressure vessel. Palladium on carbon (5%, 15 g) was added and the mixture stirred under an atmosphere of hydrogen (4 kg) for 24 hours. Catalyst was removed by filtration, and the solvents distilled off under vacuum. Crude 58 was purified by column chromatography on silica gel using chloroform as eluant to get pure 58 (4.5 g, 24.4%) as a white powder with an m.p. between 87.5-90.4° C.

$^1$H NMR (CDCl$_3$+DMSO-d$_6$) δ 1.40 (m, 4H, CH$_2$), 1.60 (m, 2H, CH$_2$), 2.20 (t, 2H, CH$_2$),3.40 (t, 2H, CH$_2$), 3.68 (s, 3H, ester), 3.94 (bs, 1H, OH), 4.50 (s, 2H, CH$_2$), 6.68 (d, 2H, Ar), 7.42 (d, 2H, Ar), 9.30 (s, 1H, NH).

EXAMPLE 59

2-[4-(6-Benzyloxyhexanoylamino)-phenoxy]-propionic acid methyl ester (59)

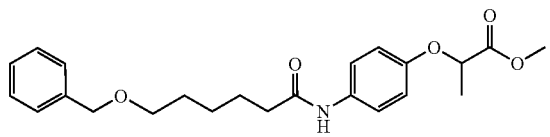

To a mixture of 2-(4-aminophenoxy)-propionic acid methyl ester 10 (20 grams, 102.44 mmol) and benzyloxy hexanoic acid (57 g, 256.43 mmol) in anhydrous dichloromethane (250 ml) at 0° C. under nitrogen atmosphere was added dropwise a solution of 1,3-dicyclohoyyl carbodiimide (74 g, 358.64 mmol) in anhyd. dichloromethane (75 ml). The reaction mixture was stirred at room temp. for 20 hrs. Solids were filtered off, the dichloromethane was washed with 5% sodium bicarbonate (2×100 ml), then water (2×100 ml), dried over sodium sulphate, and distilled to get crude 59. Crude 59 was purified by column chromatography on silica gel using chloroform as eluant to get pure 59 (15 g, 36.7%) as a light pink powder with an m.p. between 73-76.5° C.

$^1$H NMR (CDCl$_3$) δ 1.45 (m, 2H, CH$_2$), 1.60 (d, 3H, CH$_3$), 1.70 (m, 4H, CH$_2$),2.45 (t, 2H, CH$_2$), 3.45 (t, 2H, CH$_2$), 3.72 (s, 3H, Ester), 4.46 (s, 2H, CH$_2$), 4.66 (q, 1H, CH), 6.70 (d, 2H, Ar), 7.24 (m, 5H, Ar), 7.30 (d, 2H, Ar), 7.54 (s, 1H, NH)

EXAMPLE 60

2-[4-(6-Hydroxyhexanoylamino)-phenoxy]-propionic acid methyl ester (60)

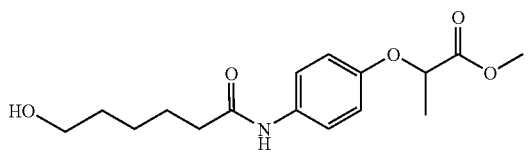

2-[4-(6-Benzyloxyhexanoylamino)-phenoxy]-propionic acid methyl ester 59 (15 g, 37.59 mmol) was dissolved in methanol (150 ml) in a pressure vessel. Palladium on carbon (50% wet, 5%, 15 g) was added and the mixture stirred under hydrogen atmosphere (4 kg) for 16 hrs. Catalyst was removed by filtration and methanol distilled off. Crude 60 was purified by column chromatography on silica gel using chloroform as eluant to get pure 60 (6 g, 51.6%) as a white powder with an m.p between 62-64.5° C.

$^1$H NMR (CDCl$_3$) δ 1.40 (m, 6H, CH$_2$), 1.54 (d, 3H, CH$_3$), 2.21 (t,2H, CH$_2$), 3.48(t,2H), CH$_2$), 3.70(s,3H,Ester), 4.66(q, 1H,CH), 6.68(d,2H,Ar), 7.36(d,2H,Ar), 8.66(s, 1H,NH)

EXAMPLE 61

6-[4-(6-Benzyloxyhexanoylamino)-phenoxy]-hexanoic acid methyl ester (61)

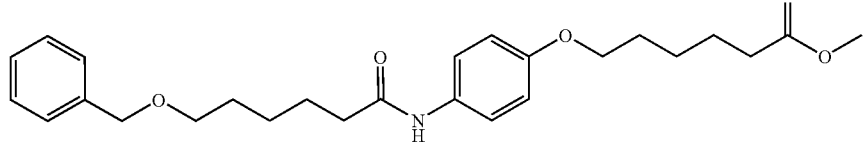

To a mixture of 6-(4-aminophenoxy)-hexanoic acid methyl ester 17 (25 grams, 105.48 mmol) and benzyloxyhexanoic acid (37.5 g, 168.7 mmol) in anhyd. dichloromethane (250 ml) at 0° C. under nitrogen atmosphere was added dropwise a solution of 1,3-dicyclohexyl carbodiimide (55 g, 266.56 mmol) in anhydrous dichloromethane (60 ml). The reaction mixture was stirred at room temperature for 16 hs. Solids were filtered off, the dichloromethane was washed with 5% sodium bicarbonate solution (2×100 ml), then water (2×100 ml), dried over sodium sulphate and distilled to get crude 61. Crude 61 was purified by column chromatography on silica gel using benzene:hexane (1:1) to get pure 61 (28 g, 60.2%) as a white powder with an m.p. between 64-65.6° C.

$^1$H NMR (CDCl$_3$) δ 1.48 (m, 2H, CH$_2$), 1.70 (m, 1OH, CH$_2$), 2.30 (m, 2H, CH$_2$), 3.48 (t, 2H, CH$_2$), 3.68 (s, 3H, Ester), 3.88 (t, 2H, CH$_2$), 4.44 (s, 2H, CH$_2$), 6.72 (d, 2H, Ar), 7.30 (m, 8H, Ar & NH)

EXAMPLE 62

6-[4-(6-Hydroxyhexanoylamino)-phenoxy]-hexanoic acid methyl ester (62)

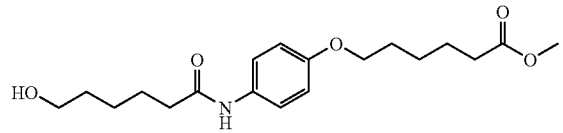

6-[4-(6-Benzyloxyhexanoylamino)-phenoxy]-hexanoic acid methyl ester 61 (10 g, 22.67 mmol) was dissolved in methanol (100 ml) in a pressure vessel. Palladium on carbon (5%, 6 grm) was added and the mixture stirred under a hydrogen atmosphere (4 kg) for 20 hrs. The catalyst was removed by filtration, and methanol distilled off. Crude 62 was purified by column chromatography on silica gel using chloroform as eluant to give pure 62 (5 g, 62.8%) as a white powder with a m.p. between 73-75.5° C.

$^1$H NMR (CDCl$_3$) δ 1.40 to 1.80 (m, 12H, CH$_2$), 2.36 (m, 4H, CH$_2$), 3.58 (t, 2H, CH$_2$), 3.64 (s, 3H, Ester), 3.88 (t, 2H, CH$_2$), 6.72 (d, 2H, Ar), 7.26(d,2H,Ar), 7.40(s, 1H,NH).

EXAMPLE 63

[4-(6-Benzyloxyhexanoylamino)phenoxy]acetic acid methoxycarbonyl methyl ester (63)

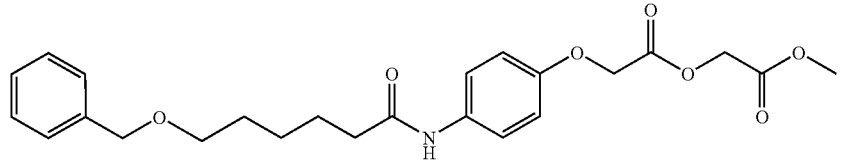

To a mixture of (4-aminophenoxy)acetic acid methoxycarbonyl methyl ester 43 (15 g, 62.76 mmol) and benzyloxyhexanoic acid (21 g, 94.47 mmol), in anhydrous dichloromethane (300 ml) at 0° C. under nitrogen atmosphere was added dropwise a solution of 1,3-dicyclohexyl carbodiimide (39 g, 189 mmol). The reaction mixture was stirred at room temp. for 18 hrs. The solids were filtered off, the dichloromethane was washed with 5% sodium bicarbonate solution (2×75 ml), then water (2×75 ml), dried over sodium sulphate, and distilled to give crude 63. Crude 63 was purified by column chromatography on silica gel using chloroform as eluant to get pure 63 (15 g, 53.9%) as a white powder with an m.p. between 71-73° C.

$^1$H NMR (CDCl$_3$) δ 1.44 (m, 2H, CH$_2$), 1.66 (m, 4H, CH$_2$), 2.30 (t, 2H, CH$_2$), 3.44 (t, 2H, CH$_2$), 3.74 (s, 3H, Ester), 4.48 (s, 2H, CH$_2$), 4.70 (s, 4H, CH$_2$), 6.80 (d, 2H, Ar), 7.30 (m, 8H, Ar & NH)

EXAMPLE 64

[4-(6-Hydroxyhexanoylamino)phenoxy]acetic acid methoxycarbonyl methyl ester (64)

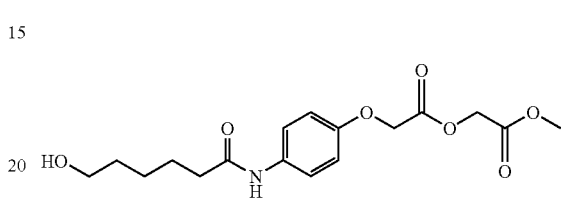

[4-(6-Benzyloxyhexanoylamino)-phenoxy]-acetic acid methoxycarbonyl methyl ester 63 (13 g, 29.34 mmol) was dissolved in dimethylformamide (100 ml) in a pressure vessel. Palladium on carbon (5%, 10 g) was added and the mixture stirred under a hydrogen atmosphere (4 kg) for 20 hrs. Catalyst was removed by filtration and dimethylformamide distilled off under vacuum. Ice water (100 ml) was added and extracted with chloroform, dried over sodium sulphate, and distilled to give crude 64. Crude 64 was purified by column chromatography on silica gel using chloroform as eluant to give 6 g of solid, which was further purified by recrystallising in chloroform: hexane (1:6) to get pure 64 (4 g, 38.6%) as a light pink powder with an m.p. between 68-70.5° C.

$^1$H NMR (CDCl$_3$) δ 1.44 (m, 2H, CH$_2$), 1.58 (m, 2H, CH$_2$), 1.74 (m, 2H, CH$_2$), 2.30 (t, 2H, CH$_2$), 2.38 (bs, 1H, OH), 3.56 (t, 2H, CH$_2$), 3.78 (s, 3H, Ester), 4.70 (s, 4H, CH$_2$), 6.80 (d, 2H, Ar), 7.48 (d, 2H, Ar), 8.74 (s, 1H, NH).

In Vitro Hydrolysis of Functionalized Phenolics

Selected compounds were examined for the rate of hydrolysis by conducting in vitro hydrolysis studies at reflux temp. (100° C.). For each experiment, 500 mg of a functionalized compound and 50 ml of pH 7.4 buffer solution (purchased from Aldrich Chemical) were charged into a 100 ml round bottom flask fitted with a condenser and the contents were refluxed. In vitro hydrolysis of the functionalized phenolics was monitored by thin layer chromatography (TLC) using corresponding starting material (original phenolic) as a control. In vitro hydrolysis was continued at reflux until the functionalized molecule hydrolyzed to the starting phenolic compound.

EXAMPLE 65

(4-Aminophenoxy)-acetic acid methoxycarbonyl methyl ester (EXAMPLE-45) was hydrolyzed in 3 hours under the above conditions.

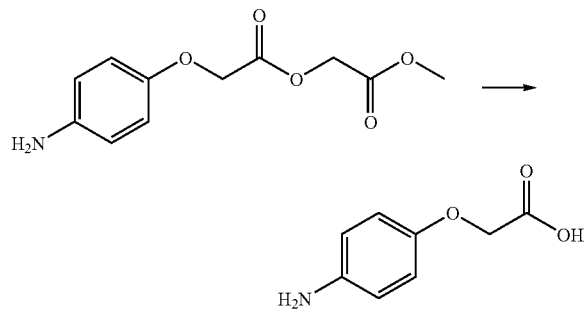

EXAMPLE 66

(4-Acetylaminophenoxy)acetic acid methoxycarbonyl methyl ester (EXAMPLE 48) was hydrolyzed in 8 hours under the above conditions

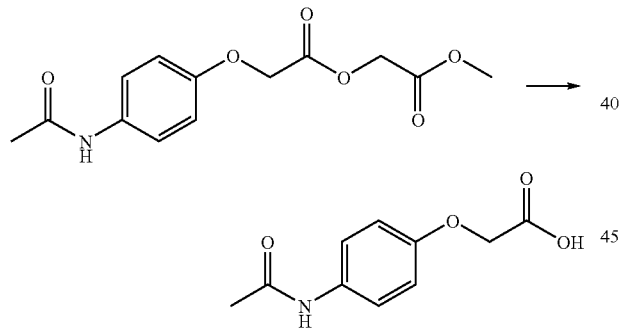

EXAMPLE 67

(4-Aminophenoxy)-acetic acid-2-[2-(4-aminophenoxy)-acetoxy]-ethyl ester (Example 25) was hydrolyzed in 11.5 hours under the above conditions.

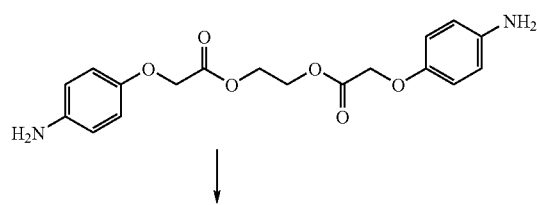

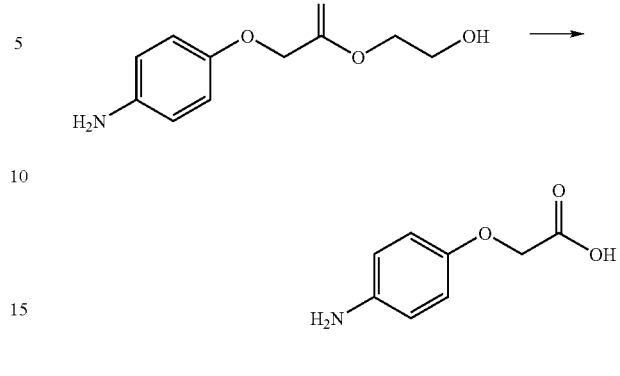

EXAMPLE 68

2-(4-Amino-phenoxy)-propionic acid 2-[2-(4-amino-phenoxy)-propionyloxy]-ethyl ester (EXAMPLE-32) was hydrolyzed in 40 hours under the above conditions.

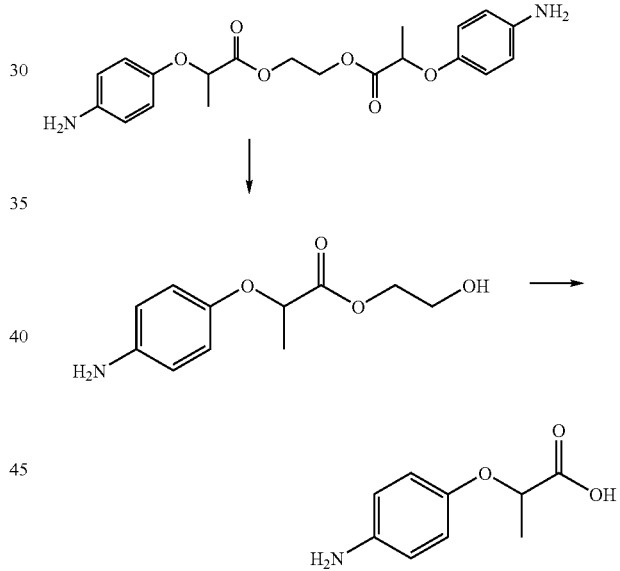

This data indicate that the polymers derived from the functionalized aminophenolics should hydrolyze. Therefore, using the functionalized aminophenolics, one can develop polymers with controlled hydrolysis profiles.

The foregoing examples and description of the preferred embodiments should be taken as illustrating, rather than as limiting, the present invention as defined by the claims. As would be readily appreciated, numerous combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. An absorbable polyurethane prepared from at least one monomer compound of the formula:

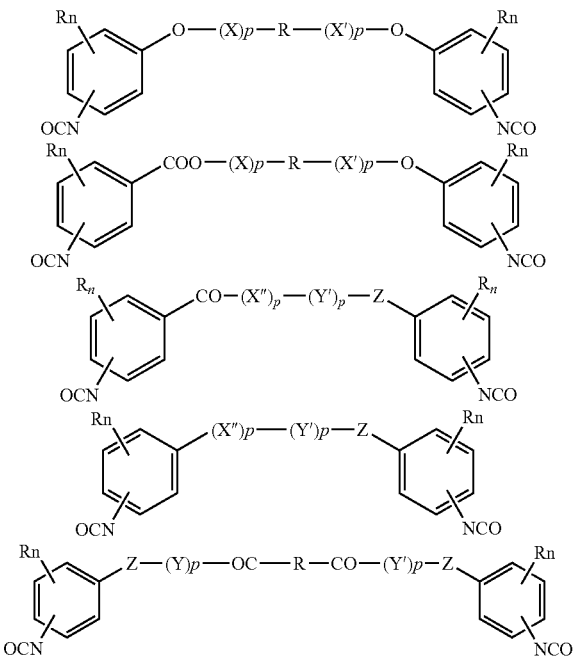

wherein each X represents a member independently selected from the group consisting of:
- —CH$_2$COO— (glycolic acid moiety);
- —CH(CH$_3$)COO— (lactic acid moiety);
- —CH$_2$CH$_2$OCH$_2$COO— (dioxanone moiety);
- —CH$_2$CH$_2$CH$_2$CH$_2$CH$_2$COO— (caprolactone moiety);
- —(CH$_2$)$_y$COO— where y is one of the numbers 2,3,4 and 6-24 inclusive, and
- —(CH$_2$CH$_2$O)$_z$CH$_2$COO— where z' is an integer between 2 and 24, inclusive;

each X' represents a member independently selected from the group consisting of:
- —OOCCH$_2$- (glycolic acid moiety);
- —OOC(CH$_3$)CH— (lactic acid moiety);
- —OOCCH$_2$OCH$_2$CH$_2$— (dioxanone moiety);
- —OOCCH$_2$CH$_2$CH$_2$CH$_2$CH$_2$- (caprolactone moiety);
- —OOC(CH$_2$)y- where y is one of the numbers 2,3,4 and 6-24 inclusive; and
- —OOCCH$_2$(OCH$_2$CH$_2$)z'- where z' is an integer between 2 and 24, inclusive;

each X" represents a member independently selected from the group consisting of:
- —OCH$_2$CO— (glycolic acid moiety);
- —OCH(CH$_3$)CO— (lactic acid moiety);
- —OCH$_2$CH$_2$OCH$_2$CO— (dioxanone moiety);
- —OCH$_2$CH$_2$CH$_2$CH$_2$CH$_2$CO— (caprolactone moiety);
- —O(CH$_2$)$_y$CO— where y is one of the numbers 2,3,4 and 6-24 inclusive; and
- —O(CH$_2$CH$_2$O)$_z$CH$_2$CO— where z' is an integer between 2 and 24, inclusive;

each Y represents a member independently selected from the group consisting of:
- —COCH$_2$O— (glycolic ester moiety);
- —COCH(CH$_3$)O— (lactic ester moiety);
- —COCH$_2$OCH$_2$CH$_2$O— (dioxanone ester moiety);
- —COCH$_2$CH$_2$CH$_2$CH$_2$CH$_2$O— (caprolactone ester moiety);
- —CO(CH$_2$)$_m$O— where m is an integer between 2-4 and 6-24 inclusive; and
- —CO CH$_2$O (CH$_2$CH$_2$O)$_n$- where n is an integer between 2 and 24, inclusive;

each Y' represents a member independently selected from the group consisting of:
- —OCH$_2$OC— (glycolic ester moiety);
- —O(CH3)CHOC— (lactic ester moiety);
- —OCH$_2$CH$_2$OCH$_2$OC— (dioxanone ester moiety);
- —OCH$_2$CH$_2$CH$_2$CH$_2$CH$_2$OC— (caprolactone ester moiety);
- —O(CH$_2$)mOC— where m is an integer between 2-4 and 6-24 inclusive; and
- —(OCH$_2$CH$_2$)nOCH$_2$OC— where n is an integer between 2 and 24 inclusive;

each R is a benzyl or an alkyl group, the alkyl group being straight-chained or branched;

each p is independently an integer between 1 and 4, inclusive;

Z is O or NH; and

Rn represents one or more members selected from the group consisting of H, alkoxy, benzyloxy, aldehyde, halogen, carboxylic acid and —NO$_2$, and Rn is attached directly to the aromatic rings or attached through an aliphatic chain.

2. A polymer according to claim 1 wherein each X is independently selected from the group consisting of:
- —CH$_2$COO— (glycolic acid moiety),
- —CH(CH$_3$)COO— (lactic acid moiety),
- —CH$_2$CH$_2$OCH$_2$COO— (dioxanone moiety), and
- —CH$_2$CH$_2$CH$_2$CH$_2$CH$_2$COO— (caprolactone moiety);

each X' represents a member independently selected from the group consisting of:
- —OOCCH$_2$- (glycolic acid moiety);
- —OOC(CH$_3$)CH— (lactic acid moiety);
- —OOCCH$_2$OCH$_2$CH$_2$- (dioxanone moiety); and
- —OOCCH$_2$CH$_2$CH$_2$CH$_2$CH$_2$- (caprolactone moiety);

each X" represents a member independently selected from the group consisting of:
- —OCH$_2$CO— (glycolic acid moiety);
- —OCH(CH$_3$)CO— (lactic acid moiety);
- —OCH$_2$CH$_2$OCH$_2$CO— (dioxanone moiety); and
- —OCH$_2$CH$_2$CH$_2$CH$_2$CH$_2$CO— (caprolactone moiety);

each Y is independently selected from the group consisting of:
- —COCH$_2$O— (glycolic ester moiety);
- —COCH(CH$_3$)O— (lactic ester moiety);
- —COCH$_2$OCH$_2$ CH$_2$O— (dioxanone ester moiety); and
- —COCH$_2$CH$_2$CH$_2$CH$_2$CH$_2$O— (caprolactone ester moiety); and each Y' represents a member independently selected from the group consisting of:
- —OCH$_2$OC— (glycolic ester moiety);
- —O(CH$_3$)CHOC— (lactic ester moiety);
- —OCH$_2$CH$_2$OCH$_2$OC— (dioxanone ester moiety); and
- —OCH$_2$CH$_2$CH$_2$CH$_2$CH$_2$OC— (caprolactone ester moiety).

3. A polymer according to claim 1, wherein an aromatic portion of said monomer compound is derived from an aminophenol, aminosalicylic acid or an aminobenzoic acid compound.

4. An article comprising a metal or polymeric substrate for mammalian tissue contact and having thereon a coating, wherein said coating comprises at least one polymer according to claim 1.

5. The article of claim 4, wherein said article is an implantable medical device.

6. An implantable medical device comprising at least one polymer according to claim 1.

7. A molded article characterized by being prepared from at least one polymer according to claim 1.

8. A controlled drug delivery system characterized by at least one polymer according to claim 1, physically admixed with a biologically or pharmacologically active agent.

9. A controlled drug delivery system characterized by a biologically or pharmacologically active agent physically embedded or dispersed into a polymeric matrix formed from at least one polymer according to claim 1.

10. A tissue scaffold having a porous structure for the attachment and proliferation of cells, either in vitro or in vivo, characterized by being formed from one least one polymer according to claim 1.

11. The polymer according to claim 1 wherein said polyurethane comprises polyester chain extender segments polymerized from at least one lactone monomer selected from the group consisting of glycolide, lactide, p-dioxanone, trimethylene carbonate and caprolactone.

12. An implantable medical device comprising at least one polymer according to claim 11.

13. A molded article characterized by being prepared from at least one polymer according to claim 11.

14. A controlled drug delivery system characterized by at least one polymer according to claim 11, physically admixed with a biologically or pharmacologically active agent.

15. A controlled drug delivery system characterized by a biologically or pharmacologically active agent physically embedded or dispersed into a polymeric matrix formed from at least one polymer according to claim 11.

16. A tissue scaffold having a porous structure for the attachment and proliferation of cells, either in vitro or in vivo, characterized by being formed from at least one polymer according to claim 11.

* * * * *